(12) United States Patent
Mitrev

(10) Patent No.: US 7,462,156 B2
(45) Date of Patent: Dec. 9, 2008

(54) REPLACEMENT AORTIC VALVE LEAFLETS AND RELATED TECHNOLOGY

(76) Inventor: Zan Mitrev, Special Hospital For Cardiosurgery, Filip, 11 Ilindeska b.b., Skopje (MK)

( * ) Notice: Subject to any disclaimer, the term of this patent is extended or adjusted under 35 U.S.C. 154(b) by 627 days.

(21) Appl. No.: 11/192,098

(22) Filed: Jul. 29, 2005

(65) Prior Publication Data

US 2006/0229716 A1 Oct. 12, 2006

Related U.S. Application Data

(60) Provisional application No. 60/670,019, filed on Apr. 11, 2005.

(51) Int. Cl.
*A61B 5/103* (2006.01)
*A61B 1/00* (2006.01)
*A61F 2/24* (2006.01)

(52) U.S. Cl. .................. 600/587; 623/2.11; 33/512

(58) Field of Classification Search .............. 600/587; 623/2.11, 912–913; 33/511–512
See application file for complete search history.

(56) References Cited

U.S. PATENT DOCUMENTS

| 4,211,241 | A | * | 7/1980 | Kaster et al. | ................ | 600/587 |
|---|---|---|---|---|---|---|
| 5,713,953 | A | | 2/1998 | Vallana et al. | | |
| 6,110,200 | A | * | 8/2000 | Hinnenkamp | ............... | 623/2.11 |
| 6,113,631 | A | | 9/2000 | Jansen | | |
| 6,328,763 | B1 | | 12/2001 | Love et al. | | |
| 6,358,277 | B1 | * | 3/2002 | Duran | ....................... | 623/2.12 |
| 6,451,054 | B1 | * | 9/2002 | Stevens | ..................... | 623/2.11 |
| 6,491,511 | B1 | | 12/2002 | Duran et al. | | |
| 6,558,417 | B2 | | 5/2003 | Peredo | | |
| 6,613,086 | B1 | | 9/2003 | Moe et al. | | |
| 6,613,087 | B1 | | 9/2003 | Healy et al. | | |
| 6,726,715 | B2 | | 4/2004 | Sutherland | | |
| 6,821,257 | B1 | * | 11/2004 | Jolley | ........................ | 600/595 |
| 6,837,902 | B2 | | 1/2005 | Nguen et al. | | |
| 7,160,322 | B2 | * | 1/2007 | Gabbay | ..................... | 623/2.36 |
| 7,357,814 | B2 | * | 4/2008 | Gabbay | ..................... | 623/2.11 |
| 2002/0077698 | A1 | | 6/2002 | Peredo | | |

(Continued)

OTHER PUBLICATIONS

"Use of the acyl azide method for cross-linking collagen-rich tissues such as pericardium", Petite et al., J Biomed Mater Res. Feb. 1990; 24 (2) :179-87.

(Continued)

*Primary Examiner*—Suzette J Gherbi
(74) *Attorney, Agent, or Firm*—Christopher Wood; Wood & Eisenberg, PLLC

(57) ABSTRACT

Replacement aortic heart leaflets and method of making the same. The replacement aortic heart leaflets of the present invention include first and second segments. The second segment is integral with, and extends from, the first segment. A virtual line L having a predetermined length corresponding to the distance between two known aortic commissures separates the first and second segments. In another aspect of the invention, the first segment has a virtual line AM of predetermined length. In another aspect of the present invention, a leaflet-measuring device is described. In another aspect of the invention, a standard set of replacement aortic leaflets is described. Methods are provided to provide replacement aortic leaflets based on traced outlines obtained from a surgically opened aortic ring.

9 Claims, 39 Drawing Sheets

U.S. PATENT DOCUMENTS

2004/0024452 A1 2/2004 Kruse et al.
2004/0138743 A1 7/2004 Myers et al.
2005/0240202 A1* 10/2005 Shennib et al. ............. 606/142
2006/0167468 A1* 7/2006 Gabbay ...................... 606/108

OTHER PUBLICATIONS

"Use of diphenylphosphorylazide for cross-linking collagen-based biomaterials", Petite et al., J Biomed Mater Res., Feb. 1994; 28 (2) :159-65.

* cited by examiner

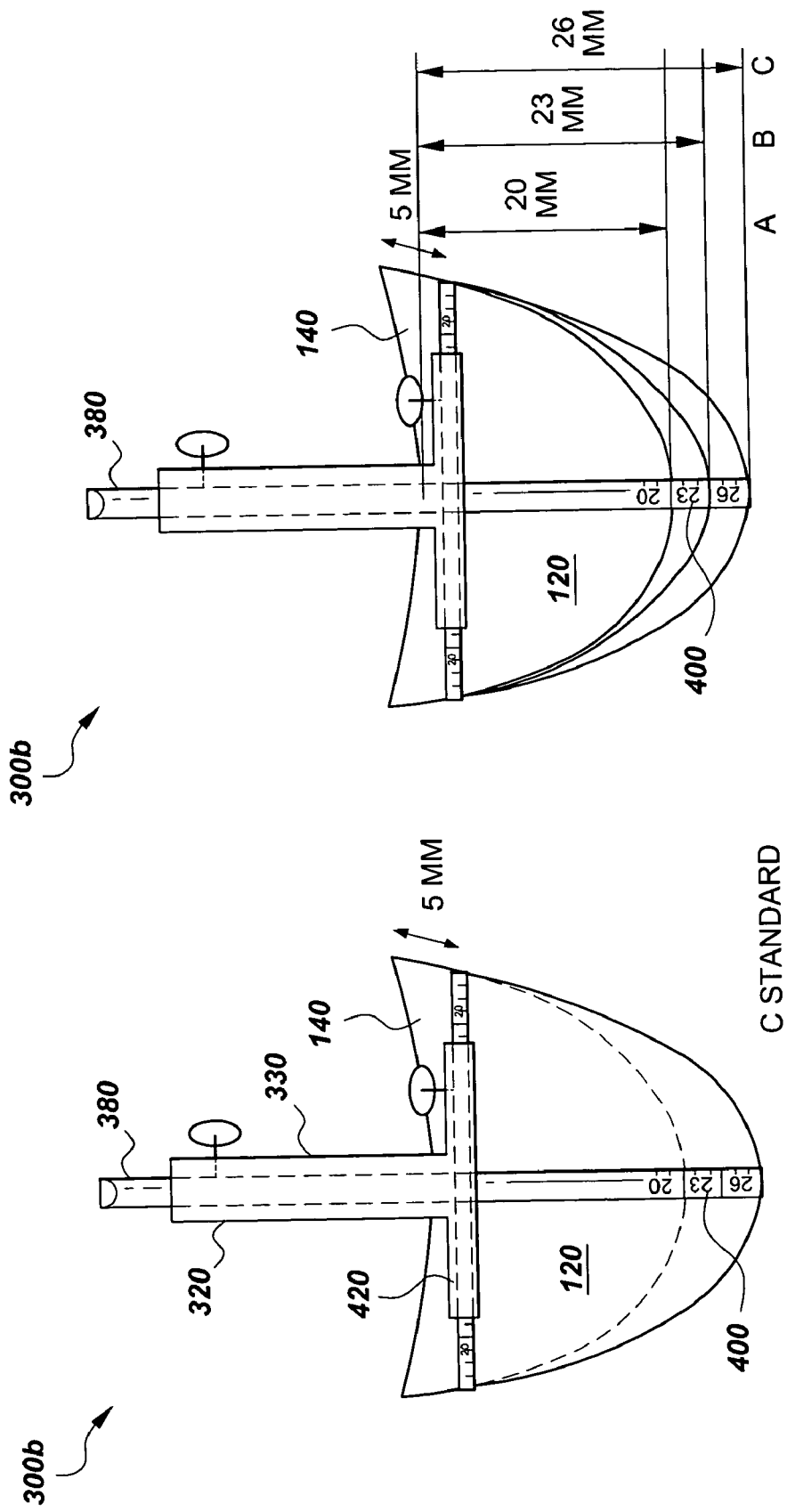

REPLACEMENT AORTIC VALVE LEAFLETS AND RELATED TECHNOLOGY

CROSS-REFERENCE TO RELATED APPLICATIONS

This application claims the benefit of priority from U.S. Provisional Patent Application Ser. No. 60/670,019, filed Apr. 11, 2005, the entire contents of which are incorporated herein by reference.

STATEMENT REGARDING FEDERALLY SPONSORED RESEARCH OR DEVELOPMENT

Not Applicable.

FIELD OF THE INVENTION

This invention relates generally to heart surgery. More specifically, the invention is an apparatus and method for aortic heart valve replacement.

BACKGROUND OF THE INVENTION

There are four valves in the heart that serve to direct blood flow through the two sides of the heart. One of these valves is the aortic valve, which is located between the left ventricle and the aorta. The aortic valve plays a vital role in helping to direct oxygenated blood from the lungs through the left side of the heart and into the aorta for distribution to the body. Like the other major heart valves, the aortic valve is a passive structure in that it does not expend any energy in opening and closing. More specifically, the aortic valve has three leaflets that open and close in response to differential pressures on either side of the aortic valve. The aortic valve, along with the pulmonary valve, is referred to as a "semi-lunar valve" because of its unique appearance of its leaflets, which are shaped somewhat like a half-moon and are sometimes called "cusps". The aortic valve, along with the pulmonary valve, has three cusps.

Heart valves, including the aortic valve, can exhibit abnormal anatomy and function as a result of congenital or acquired valve disease. Congenital valve abnormalities may be well tolerated for many years only to develop a life-threatening problem in an elderly patient, or may be so severe that emergency surgery is required within the first few hours of life. Acquired valve disease may result from causes such as rheumatic fever, degenerative disorders of the valve tissue, bacterial or fungal infections, and trauma.

Since the aortic valve is a passive structure that simply opens and closes in response to differential pressures on either side of the valve, the problems that can develop can be classified into two categories: (1) stenosis, in which the aortic valve does not open properly, and (2) insufficiency (also called regurgitation), in which the aortic valve does not close properly. Stenosis and insufficiency can occur concomitantly. Both of these abnormalities increase the workload placed on the heart. The severity of this increased stress on the heart and the patient, and the heart's ability to adapt to it, determine whether an abnormal aortic valve or its individual leaflets have to be surgically replaced, most often by replacing the entire valve with an artificial valve such as an artificial mechanical valve or an artificial tissue valve.

On information and belief, the currently available replacement options cannot duplicate the advantages of native (natural) heart valves. Some of the available mechanical valves tend to be very durable, but are problematic in that they are thrombogenic and exhibit relatively poor hemodynamic properties. In addition, mechanical valve replacements tend to replace in total all three leaflets of the aortic valve including undamaged and adequately performing aortic leaflets or cusps. Some of the available artificial tissue valves may have relatively low thrombogenicity, but often do not exhibit hemodynamic properties that approach the advantageous hemodynamic performance of a native valve. Thus, there is a need for an apparatus and method for more specific replacement of aortic leaflets, which also offers the flexibility of replacing individual leaflets.

A description of the prior art follows.

U.S. Publication No. 20020077698, published Jun. 20, 2002 (issued May 6, 2003 as U.S. Pat. No. 6,558,417) to Peredo, describes a semi-lunar stentless valve formed entirely of biological tissue. The Peredo valve has a plurality of leaflets that are joined to form an annulus and coapt to form a one-way valve. The leaflets are described as having the capability to open fully to minimize obstruction. A narrow rim of tissue is provided over commissures where the leaflets join around a base of the valve for a serving ring. According to the Peredo '698 patent publication, the valves can be sutured to heart tissue wall in a single suture row.

U.S. Pat. No. 6,328,763, issued to Love et al., describes a method of reconstructing a three-dimensional semi-lunar heart valve, or portion thereof based on optimized geometry of a tissue pattern for semi-lunar heart valve reconstruction. In one described embodiment, the two-dimensional valve tissue pattern comprises a two-dimensional configuration developed and optimized by employing, in part, the anatomy of a three-dimensional human heart valve, and the two-dimensional configuration delimits a two dimensional area that corresponds to the shape of tissue to be used in the repair of at least one leaflet of a circulatory system semi-lunar valve, wherein the configuration delimits at least one segment, and up to all three segments, of a three segment "trefoil" shape.

Geometric optimization of a tissue pattern for semi-lunar valve reconstruction was also described in an article published in November, 1999 (Hanlon J G, Suggit R W, Gibbs E, McMeeking R M, Love J W, *J Heart Valve Dis.*, November 1999; 8(6): 609-13). The methodology included computer-assisted design (CAD) to create an optimized leaflet geometry based on published dimensions for normal human aortic valves. In contrast, the Applicant's invention as claimed takes into account the actual dimensions of the aortic valve or aortic leaflets.

Pericardium tissue proved useful in repairing heart valves, but such materials were often attacked by the patient's immune system. Medical workers such as Love suggested using autologous pericardium, treated with a brief immersion in a glutaraldehyde (GA) solution, for use in an autologous tissue replacement for heart valves (Love et al., "Rapid intraoperative fabrication of an autogenous tissue heart valve: A new technique," Proceedings of the Third International Symposium on Cardiac Bioprostheses 691-698 (1986)). Later, Love reported that glutaraldehyde treated autologous pericardium, does not thicken or shrink, is resistant to calcific degeneration, and is durable beyond 25 equivalent years in the accelerated life tester. (Love et al., "Experimental evaluation of an autologous tissue heart valve. Journal of Heart Valve Disease," 1992; 1232-241). However, while antigenicity issues were reduced using glutaraldehyde treated pericardium and hemodynamic (blood flow) properties were improved over mechanical valve replacements, the optimum design of aortic leaflets has remained an issue. The terms "GA" and "glutaraldehyde" are hereinafter regarded as equivalent terms.

U.S. Pat. No. 6,726,715, issued Apr. 27, 2004 to Sutherland, describes a heart valve prosthesis for use as an aortic or pulmonary replacement valve, or as a mitral or tricuspid valve. The '715 heart valve includes leaflets that are reinforced with oriented fiber components in a laminated composite, in which the fiber-reinforcing materials are oriented to match lines of stress to provide a long-lived valve that provides strength at points of maximal stress that have hitherto been foci for material failure. In a preferred embodiment involving a stentless valve, the reinforcing materials are described as optimized in terms of the density and orientation of the fibers in the composite materials to extend the life of a stentless valve.

U.S. Publication No. 20040138743, published Jul. 15, 2004 to Myers et al., describes a tubular prosthetic semi-lunar or atrioventricular heart valve that is said to be formed by cutting flat, flexible leaflets according to a pattern. The valve is constructed by aligning the side edges of adjacent leaflets so that the leaflet inner faces engage each other, and suturing the leaflets together with successive stitches along a fold line adjacent the side edges. The stitches are placed successively from a proximal in-flow end of each leaflet toward a distal out-flow end. During operation, when the leaflets open and close, the leaflets fold along the fold line. Distal tabs extend beyond the distal end of each leaflet. The successive stitches terminate proximal of the distal tab portion so that no locked stitches are placed along the distal portion of the fold line. The tab portions of adjacent leaflets are folded over each other and sewn together to form commissural attachment tabs. The commissural tabs provide commissural attachment points to accommodate sutures and the like in order to secure the tab to a vessel wall, if a semi-lunar valve, and papillary muscles and/or chordae tendineae if an atrioventricular valve.

U.S. Pat. No. 6,837,902, issued Jan. 4, 2005 to Nguyen et al., describes heart valve leaflet selection methods and apparatuses which subject individual leaflets to loads and measure the resulting deflection to more reliably group leaflets of similar physical characteristics for later assembly in prosthetic heart valves. The deflection testing may be accomplished using a variety of test set ups that are designed to impart a load on the leaflet, which simulates the actual loading within a heart valve. The results from a number of deflection tests are used to categorize individual leaflets, which data can be combined with other data regarding the characteristics of the leaflet to better select leaflets for assembly into a multi-leaflet heart valve. In one embodiment, the deflection test is combined with an intrinsic load test, and leaflets having similar deflection and intrinsic load values used in the same heart valve. One apparatus for testing the leaflets includes a frame for securing the arcuate cusp of the leaflet while the straight coapting edge remains free, to simulate the actual leaflet mounting configuration within the heart valve prosthesis. The frame may include a lower portion having a recess for the leaflet and plurality of receptor holes around the peripheral edge of the recess, and an upper portion having a plurality of needles, which extend downward through the leaflet and into the receptor holes and secure the edges of the leaflet.

U.S. Pat. No. 6,613,087, issued Sep. 2, 2003 to Healy et al., describes a prosthetic stentless aortic tissue valve includes a substantially annular valve body having a leaflet carried therein for occluding blood flow therethrough. A root extends generally coaxially from the valve body. Visual marking are provided on the root and act as a sculpting guide for a surgeon during implantation of the prosthetic heart valve to sculpt portions of sinus areas of the root.

U.S. Pat. No. 6,613,086, issued Sep. 2, 2003 to Moe et al., describes a tri-leaflet prosthetic cardiac valve with leaflets having an analytic shape in a selected position. The leaflets are connected to a valve body at attachment curves. The shape of the leaflet is selected from a set of geometries that can be represented mathematically. The attachment curve is selected to improve the durability of the tri-leaflet valve by moving the point of maximum loaded stress along the attachment curve away from the commissures. An inner wall of the valve body is given a non-circular shape near the attachment curve, the shape of the inner wall corresponding to the attachment curve. Also, a method of making a valve by selecting an analytic leaflet shape, selecting an attachment curve to improve durability of the valve by moving the point of maximum loaded stress along the attachment curve away from the commissures, and forming a valve body to support one or more leaflets, the valve body having a non-circular inner wall conforming to the attachment curve.

U.S. Pat. No. 6,491,511, issued Dec. 10, 2002 to Duran et al., describes a pair of templates that form a mold for substantially flat biological membranes to shape the membrane into a configuration that, after trimming of excess tissue, is adapted for forming a replacement aortic, pulmonary, tricuspid or mitral heart valve. Each template has three members joined to another laterally, with each member configured to form, together with its mating member, the mold for one leaflet or cusp of the replacement heart valve. The negative template has concave surfaces for each member and the positive template has convex surfaces that mate with the concave surfaces of the first template. Each of the templates is made of thin, shell like material and has beveled edges. The biological membrane is placed between the mating convex and concave surfaces of the two templates assembled to one another to form the membrane into the configuration of the three leaflets of the replacement heart valve.

U.S. Pat. No. 6,113,631, issued Sep. 5, 2000 to Jansen, describes a mitral valve prosthesis that consists of a support housing (stent) with a base ring that bears at least two stays which substantially extend in the ring axis direction and are connected by curved wall for securing two flexible cusps. In order to obtain as uniform and reduced forces as possible between the cusps and the support housing, the connection lines between the cusps and the top inner edge of the wall lie each in a plane.

U.S. Pat. No. 5,713,953, issued Feb. 3, 1998 to Vallana et al., describes a stentless prosthesis that is made completely from material, for example bovine pericardium, other than valve material. A projection of the valve sleeve allows reparatory operations on surrounding tissues.

None of the above inventions and patents, taken either singly or in combination, is seen to describe the instant invention as claimed.

SUMMARY OF THE INVENTION

Non-native aortic heart leaflets and method of making the same. The non-native aortic heart leaflets of the present invention include first and second segments. The second segment is integral with, and extends from, the first segment. A virtual line L having a predetermined length corresponding to the distance between two known aortic commissures separates the first and second segments. In another aspect of the invention, the first segment has a virtual line AM of predetermined length. The non-native leaflets can be made of any suitable material such as glutaraldehyde treated horse pericardium tissue. In another aspect of the present invention, a leaflet-measuring device is described. The leaflet measuring device is designed to measure AM and/or L with respect to a selected leaflet and/or the AM and/or L measurements with respect to a patient's aortic valve. In another aspect of the invention, a standard set of replacement aortic leaflets is described. Methods are provided to provide replacement aortic leaflets based on traced outlines obtained from a surgically opened aortic ring.

BRIEF DESCRIPTION OF THE DRAWINGS

FIGS. 21 through 24 show the measuring device of FIG. 19 being used to measure out the dimensions of various non-native aortic leaflets.

Similar reference characters denote corresponding features consistently throughout the attached drawings.

DETAILED DESCRIPTION OF THE PREFERRED EMBODIMENTS

Figure 1A:
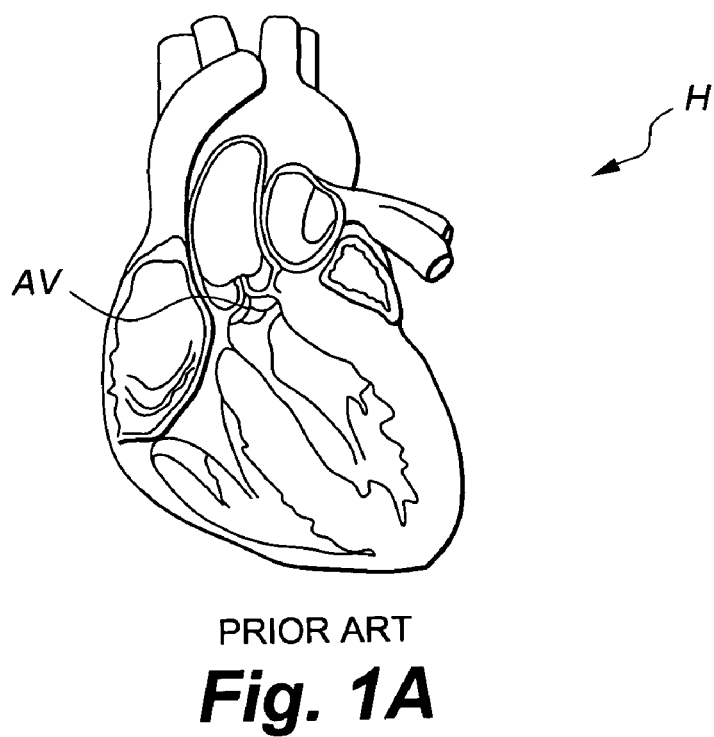
FIG. 1A shows a heart with a normal aortic valve.

This invention is an apparatus and method for replacing one or more diseased or otherwise dysfunctional leaflets in an aortic heart valve. The leaflets of the invention are attached directly onto a patient's native aortic ring to provide good hemodynamic performance without the well-known negative incumbencies associated with artificial aortic valves.

A replacement leaflet of the present invention is indicated generally by the numeral 100.

The term "patient" as used herein is intended to cover any type of patient of interest to man that can benefit from aortic leaflet replacement surgery, such as, but not limited to: human patients in need of aortic leaflet replacement surgery; animals having diseased aortic valves and under the care of, for example, a veterinary cardiologist; the domestic cat; domestic dog breeds such as, but not limited to, small-breed older dogs (e.g., the Miniature Poodle, Shetland Sheepdog, Lhasa Apsos, Dachshund, and Cocker Spaniel), larger breeds (such as the German Shepherd); horses such as a pet horse, race horse, stud horse, etc.; important farm animals such as a bull used for breeding and/or sperm collection; and zoo or amusement park animals such as the elephant, bear, rhinoceros, giraffe, wolf, lion, tiger, goat, zebra, dolphins, whales (e.g., the beluga whale and killer whale), and fur seal.

The leaflets 100 of the present invention are non-native leaflets, meaning that the leaflets 100 are intended to replace one or more of a patient's native (i.e., natural) aortic leaflets. Thus, the leaflets 100 of the present invention can be regarded as replacement aortic leaflets.

The replacement leaflets of the invention can be a xenograft, allograft or autograft, biosynthetic tissue or combinations thereof. The leaflets of the present invention can be made from any suitable collagen-rich tissue such as pericardium. The pericardium can be obtained from any suitable source such as, but not limited to, mammalian pericardium, e.g., equine (horse), kangaroo, human (e.g., cadaver), bovine or porcine pericardium. Given that the patient can be human or nonhuman, other sources of pericardium include, but are not limited to: dog, cat, tiger, lion, rhinoceros, bear, killer whale, elephant, or giraffe. Essentially any suitable source of mammalian pericardium can be used to construct leaflets of the present invention. The preferred source of pericardium for a human patient is equine pericardium treated with a cross-linking agent, such as glutaraldehyde, hydrazine or diphenylphosphorylazide solution, to minimize biodegradation of the replacement leaflet 100. Any suitable thickness of pericardium tissue can be used; with practice, a heart surgeon can decide for him/herself a preferred thickness of pericardium tissue. For example, if horse (equine) pericardium tissue is used, a heart surgeon may prefer that the equine pericardium is in the form of a sheet with a thickness in the range between about 0.3 mm and 0.6 mm, and more preferably about 0.4 mm in thickness; if cow (bovine) pericardium tissue is used, a heart surgeon may prefer that the bovine pericardium has a thickness in the range between about 0.6 mm and 0.8 mm.

Other processing can be performed to the pericardium tissue before attaching the leaflet of the invention to the aortic annuli or ring between two commissures. Other processing can include cutting and trimming of the pericardium tissue, sterilizing the tissue, associating the tissue with one or more desirable compositions, such as anticalcification agents and the like. Cutting and trimming can be done before or after treating the pericardium tissue with cross-linking agent. An appropriate medical worker can perform final trimming or cutting of pericardium tissue during, or just prior to, surgery. Glutaraldehyde treated pericardium is preferred, such as glutaraldehyde treated equine pericardium. Glutaraldehyde treated equine pericardium can be cut and trimmed into a desired leaflet shape and size, and then stored for later use, or trimmed and cut into the appropriate leaflet shape just prior to attaching the leaflet shape to a patient's native aortic ring.

After any preliminary processing and/or storage is completed, the tissue can be cross-linked. If desired, the cross-linking step can be performed while the pericardium tissue is in contact with a curved surface to provide a contoured shape as described in U.S. Publication Number 20040024452 published Feb. 5, 2005 to Kruse et al. The '452 Kruse et al. publication is herein incorporated by reference in its entirety.

Alternatively, the cross-linking step can be performed while the pericardium is not in contact with a curved surface to provide flexible tanned pericardium that can be laid out flat and easily cut to establish predetermined dimensions, especially the length of virtual line L (shown in dashed lines, e.g., see FIG. 2A), which is chosen to correspond to the actual distance between two aortic commissures of interest as determined by, for example, echocardiography, or any suitable future imaging technique, or any present imaging technique that is not, as yet, widely available.

A non-limiting example of treated pericardium tissue is equine pericardium that has been pretreated for about 10 minutes in dilute cross-linking agent such as 0.625% glutaraldehyde solution buffered to a pH of 7.4. As will be appreciated by those skilled in the art, the exact method of treating or processing pericardium tissue to reduce interaction with the immune system of the patient can vary without detracting from the spirit of the invention as claimed. For example, pericardium tissue can be cross-linked by spraying a cross-linking solution onto the tissue as described in the '452 Kruse et al. publication. Alternatively, cross-linking can be achieved via the formation of acyl azide groups on methylated carboxyl groups of collagen using hydrazine and nitrous acid as described in Petite et al. ("Use of the acyl azide method for cross-linking collagen-rich tissues such as pericardium", J Biomed Mater Res., February 1990; 24(2): 179-87). The 1990 Petite et al. article is herein incorporated by reference in its entirety. Another cross-linking agent is diphenylphosphorylazide (DPPA) in the form of 0.5% DPPA solution, which can be used to form acyl azide groups to cross-link collagen-based biomaterials such as pericardium tissue as described by Petite et al. ("Use of diphenylphosphorylazide for cross-linking collagen-based biomaterials", J Biomed Mater Res., February 1994; 28(2): 159-65). The 1994 Petite et al. article is herein incorporated by reference in its entirety.

Figure 1B:
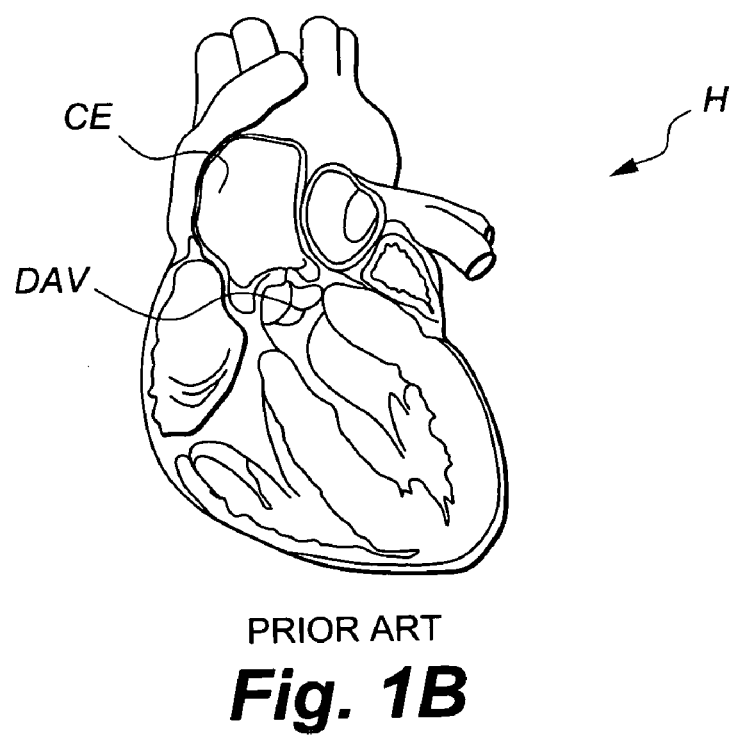
FIG. 1B shows a heart with a diseased aortic valve.

Referring to FIGS. 1A and 1B. FIG. 1A shows a heart H with a normal aortic valve AV. FIG. 1B shows a heart H with a diseased aortic valve DAV. More specifically, FIG. 1B shows pathologic deformation of the aorta ascendance in a patient's heart with aortic stenosis. Typically, chamber enlargement CE (shown in FIG. 1B) occurs on one side of the affected valve.

Figure 2A:
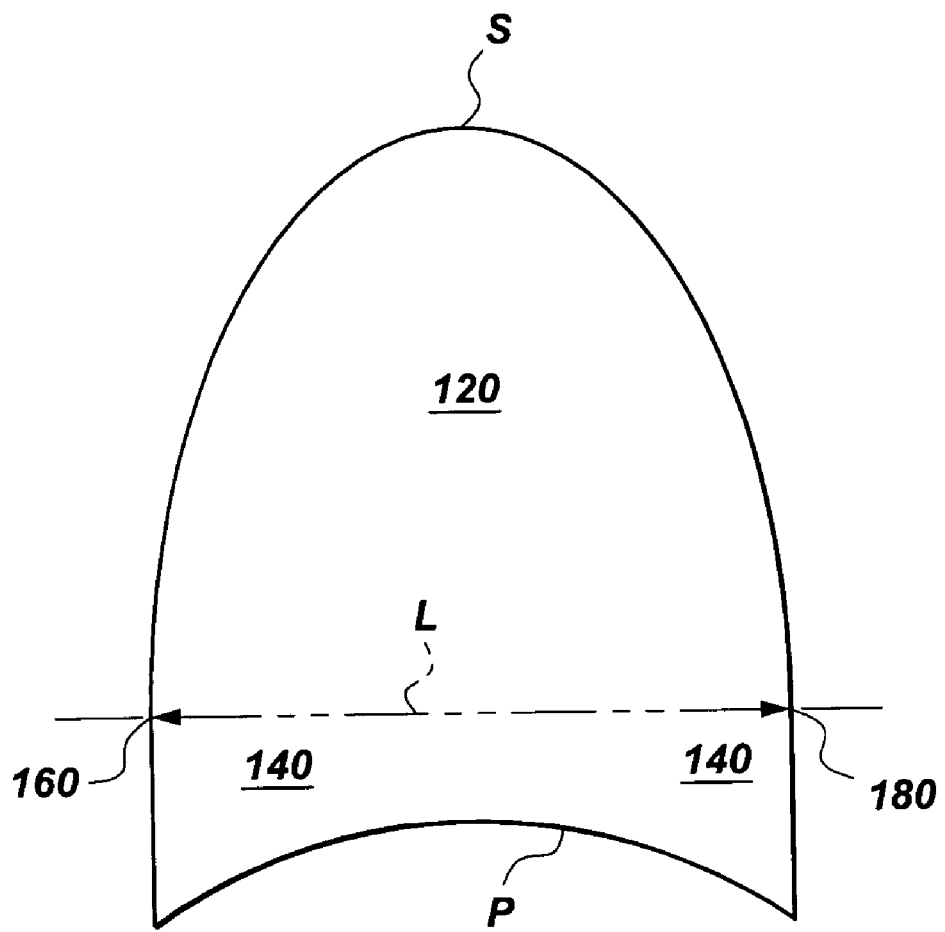
FIG. 2A shows an exemplary leaflet of the present invention.
Figure 2B:
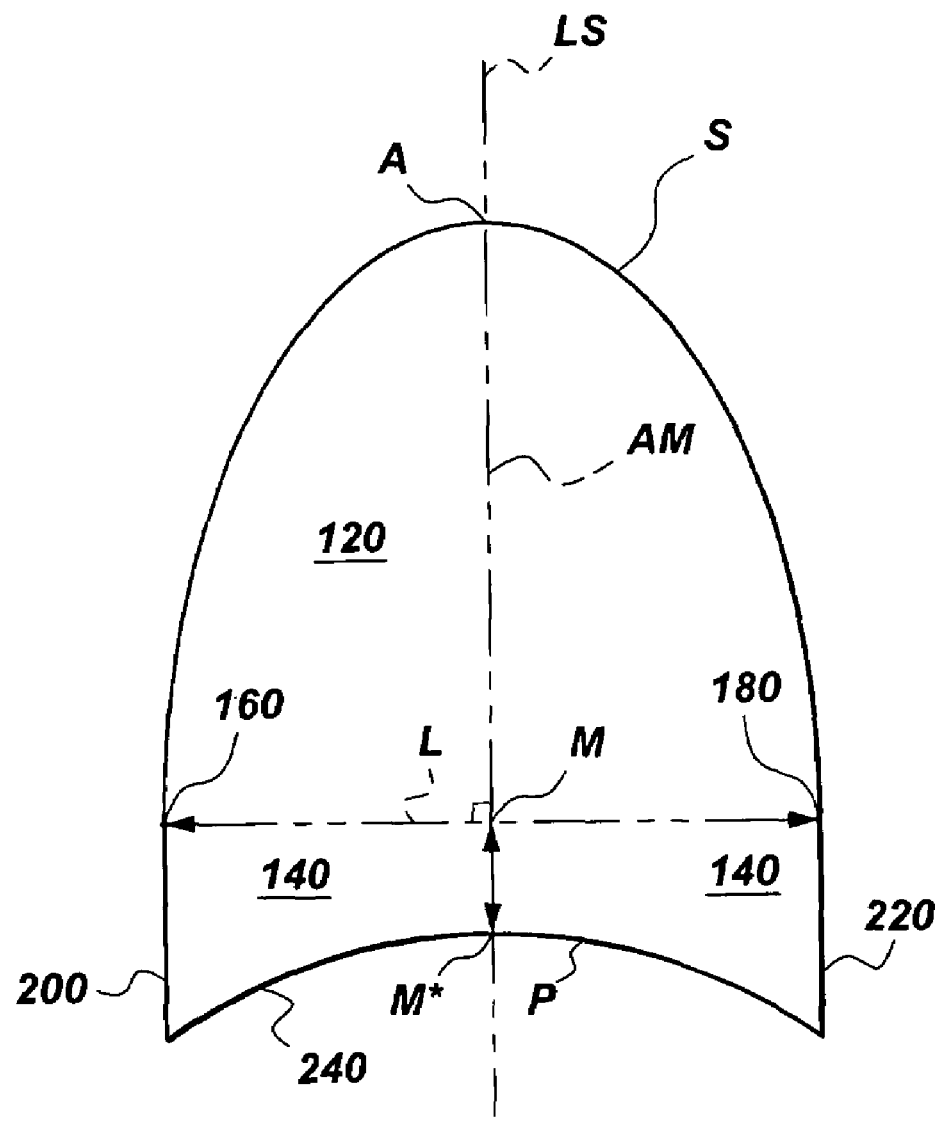
FIG. 2B shows an exemplary leaflet of the present invention.
Figure 2C:
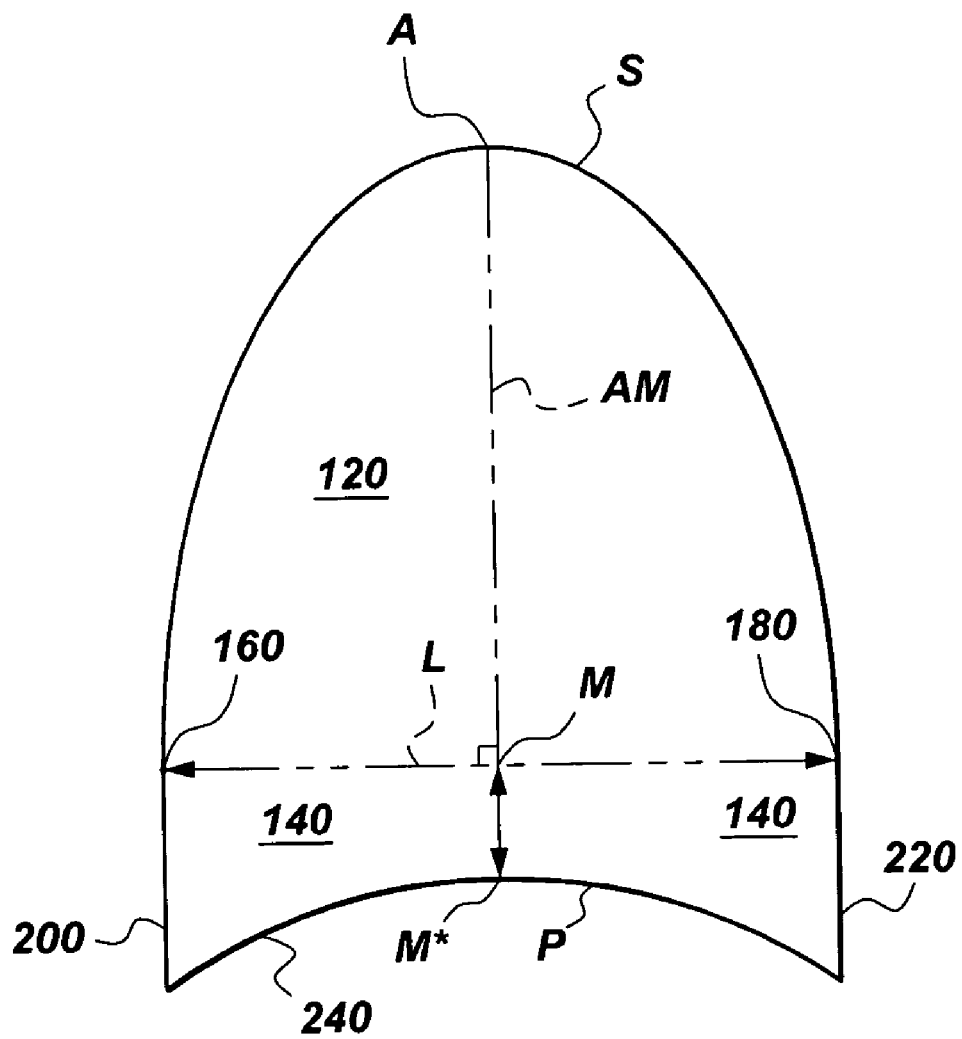
FIG. 2C shows an exemplary leaflet of the present invention.
Figure 2D:
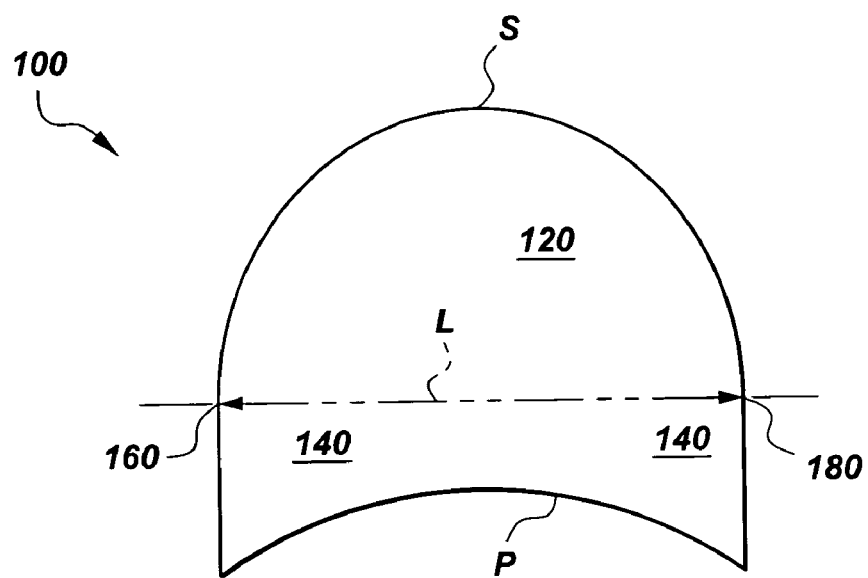
FIG. 2D shows an exemplary leaflet of the present invention.
Figure 2E:
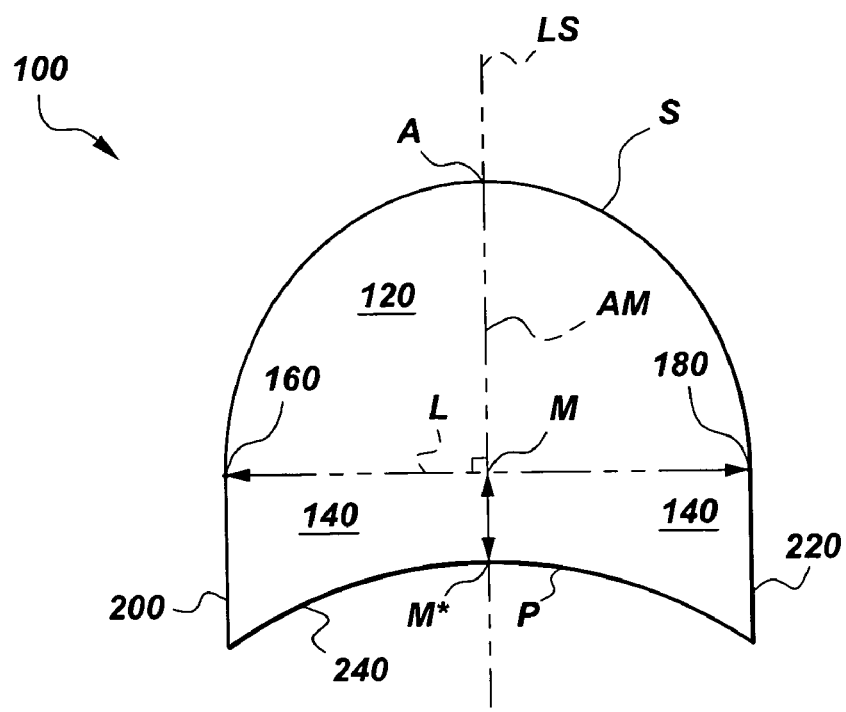
FIG. 2E shows an exemplary leaflet of the present invention.

FIGS. 2A, 2B and 2C show an exemplary replacement leaflet 100 of the present invention. The exemplary replacement leaflet 100 includes a generally curved segment 120 integral with a border segment 140, i.e., the overlap segment 140 is integral with and extends from segment 120. The segments 120 and 140 are respectively bounded by first and second peripheries S and P. The first periphery S is a generally curved periphery and is essentially attached at an appropriate time to a section of aortic ring AR between two aortic commissures of interest. The second periphery P is a borderline periphery that borders the borderline peripheries of adjacent native or non-native replacement leaflet(s) 100 of the present invention, which in unison cooperatively open and close the patient's aortic valve AV (see, e.g., FIGS. 9 and 10). First periphery S includes midpoint A (shown in FIGS. 2B and 2C). A virtual line L separates segments 120 and 140 (virtual line L is shown as a dashed line; virtual line L represents the inter-commissural dimension, i.e., the distance between two selected aortic commissures such as 260a and 260b shown in FIG. 3B); L is defined by opposite end points 160 and 180, wherein L includes midpoint M. A virtual line AM is shown in dashed lines between midpoint A and midpoint M (see FIGS. 2B and 2C), i.e., virtual line AM approximately bisects segment 120; more specifically, midpoint A on first periphery S is merely the intercept point between virtual perpendicular line AM and periphery S. In the exemplary example, first periphery S is defined by end points 160 and 180 (represented by virtual line L) and virtual line AM; and second periphery P is defined by end points 160 and 180 (i.e., virtual line L), opposite sides 200 and 220 and front side 240. However, it will be understood that the second periphery P can map out an irregular shape and therefore may not include regular sides such as sides 200 and 220. Specifically, a heart surgeon may stretch or trim segment 120 or 140 thereby altering the path followed by the first S or second periphery P (see FIG. 4A).

Figure 9:
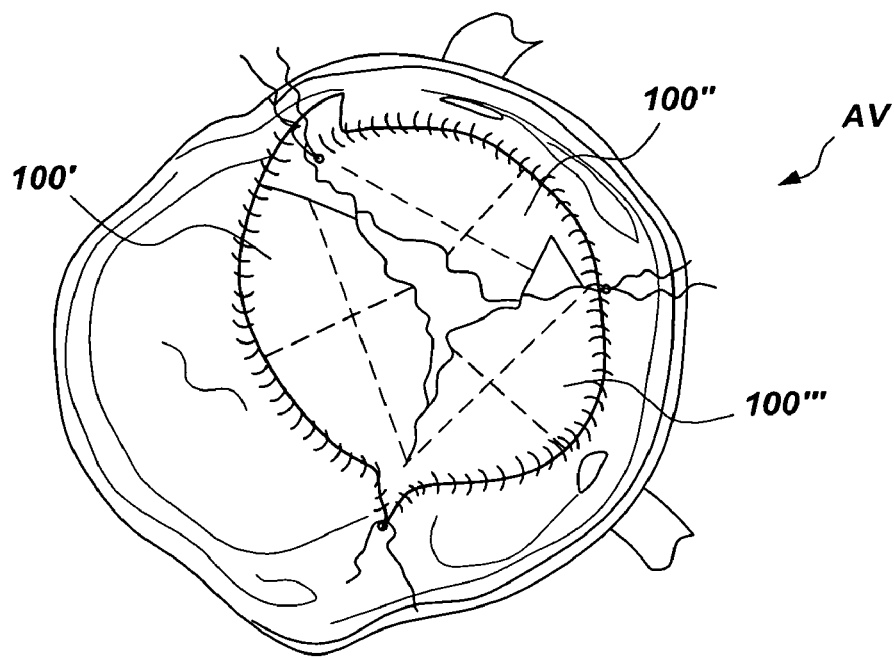
FIG. 9 shows the leaflets of FIG. 5 fitted to a patient's aortic ring, wherein the leaflets are shown in an open state.
Figure 10:
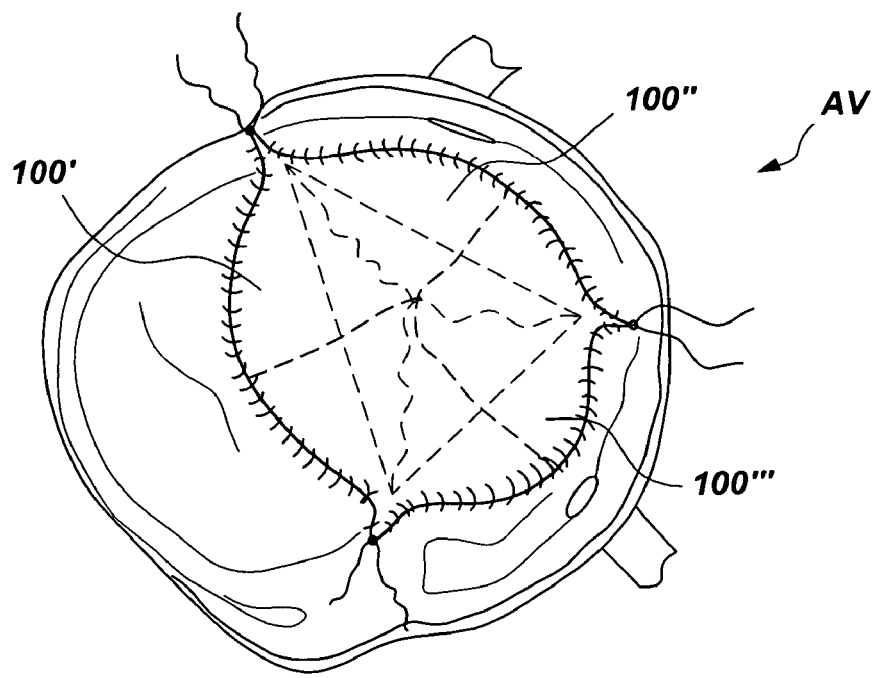
FIG. 10 shows the leaflets of FIG. 5 fitted to a patient's aortic ring, wherein the leaflets are shown in a closed state.
Figure 11:
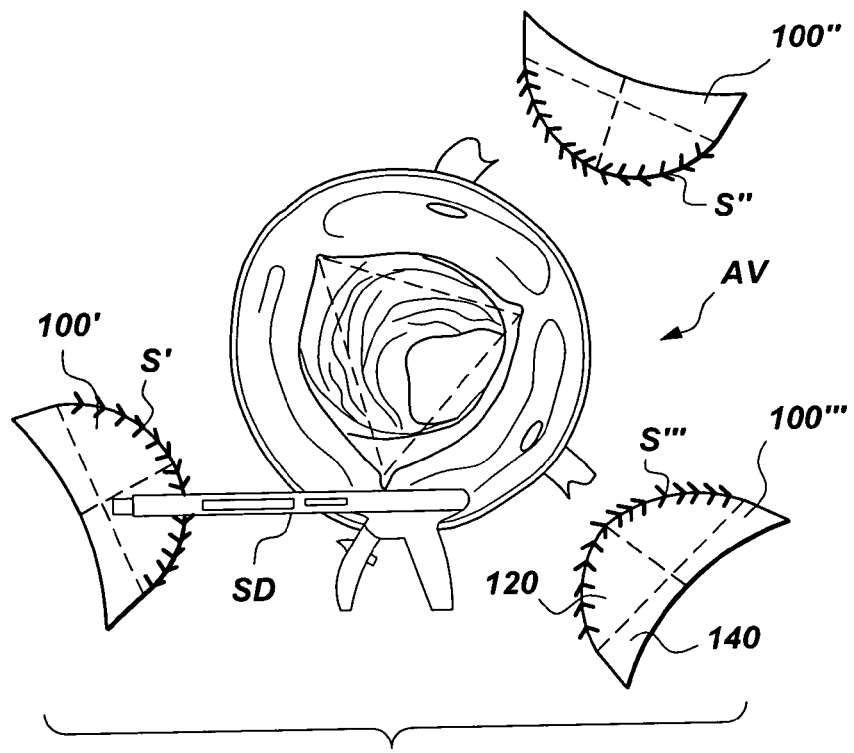
FIG. 11 shows three non-native leaflets about to be stapled to a patient's aortic valve, according to the present invention.
Figure 12:
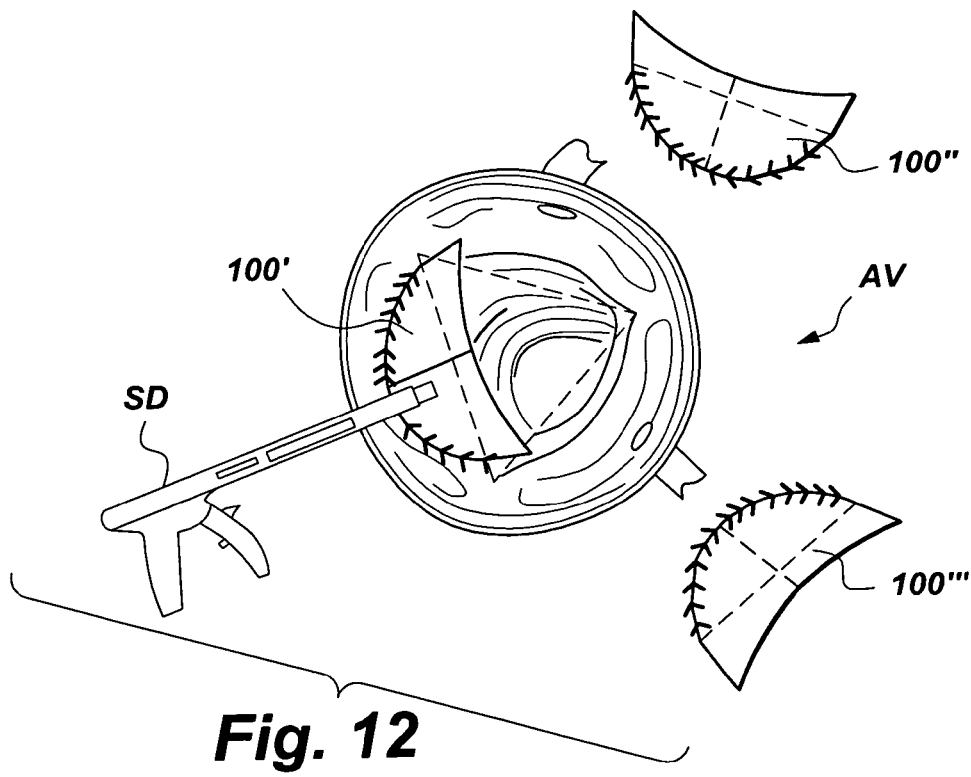
FIG. 12 shows a step in attaching the non-native leaflets of FIG. 11 to a patient's aortic ring.
Figure 13:
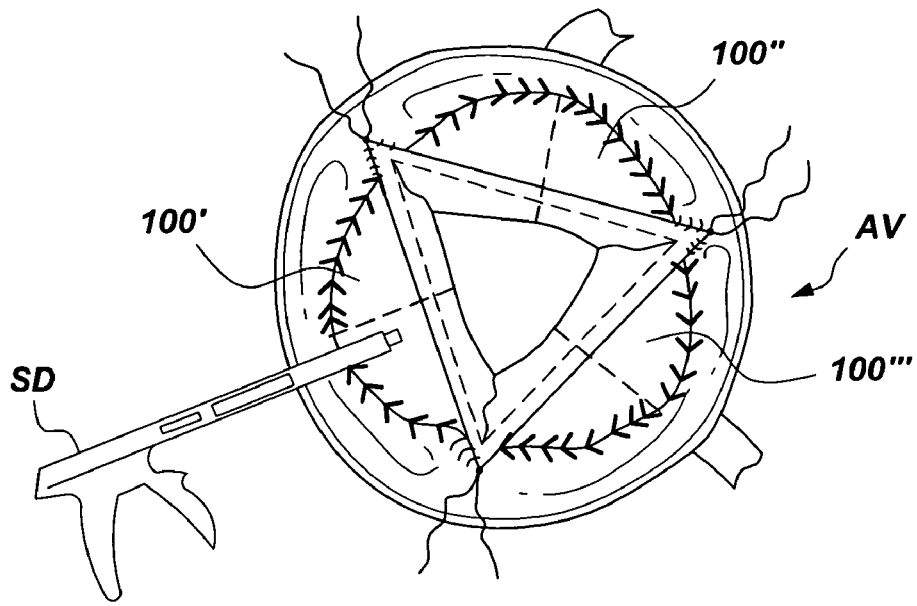
FIG. 13 shows the leaflets of FIG. 11 fitted to a patient's aortic ring, wherein the leaflets are shown in an open state.
Figure 14:
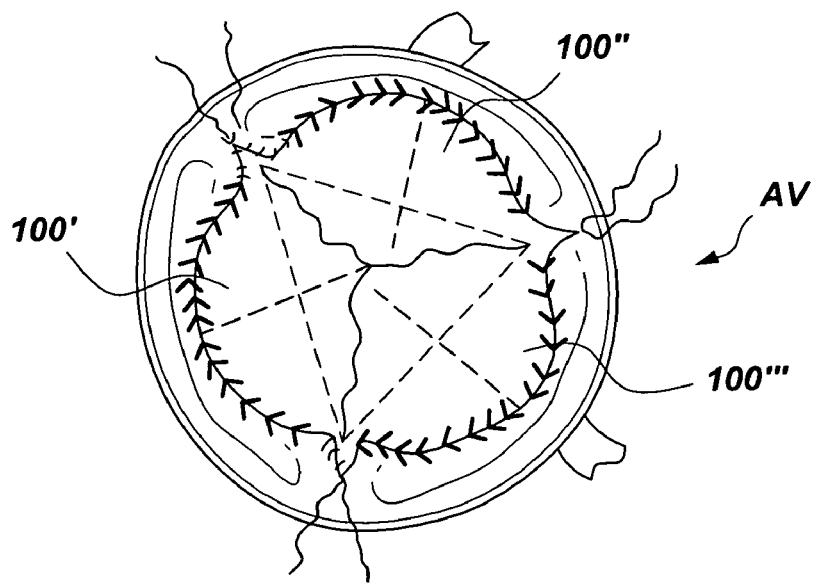
FIG. 14 shows the leaflets of FIG. 11 fitted to a patient's aortic ring, wherein the leaflets are shown in a closed state.
Figure 15:
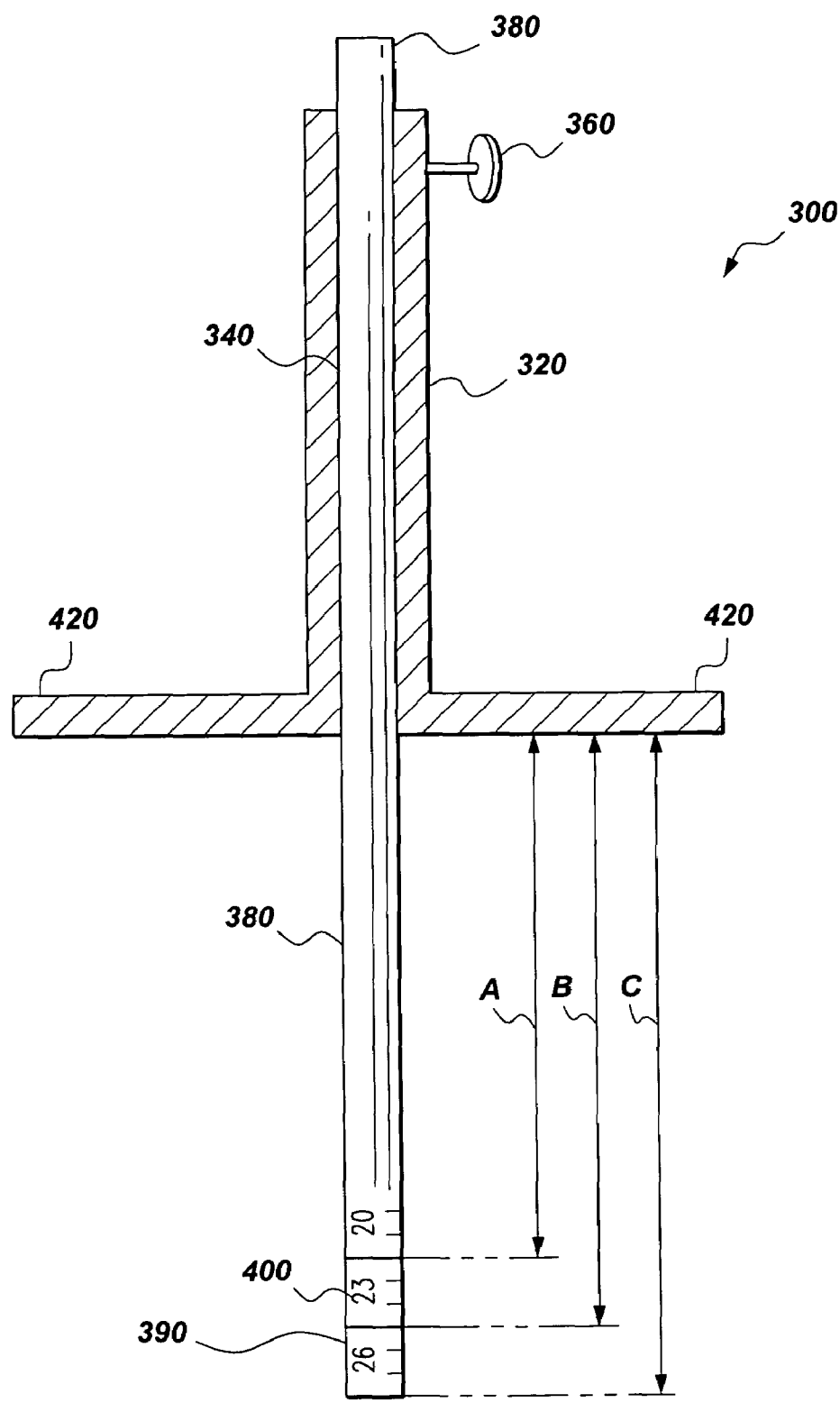
FIG. 15 shows a non-native leaflet-measuring device, according to the invention.
Figure 16:
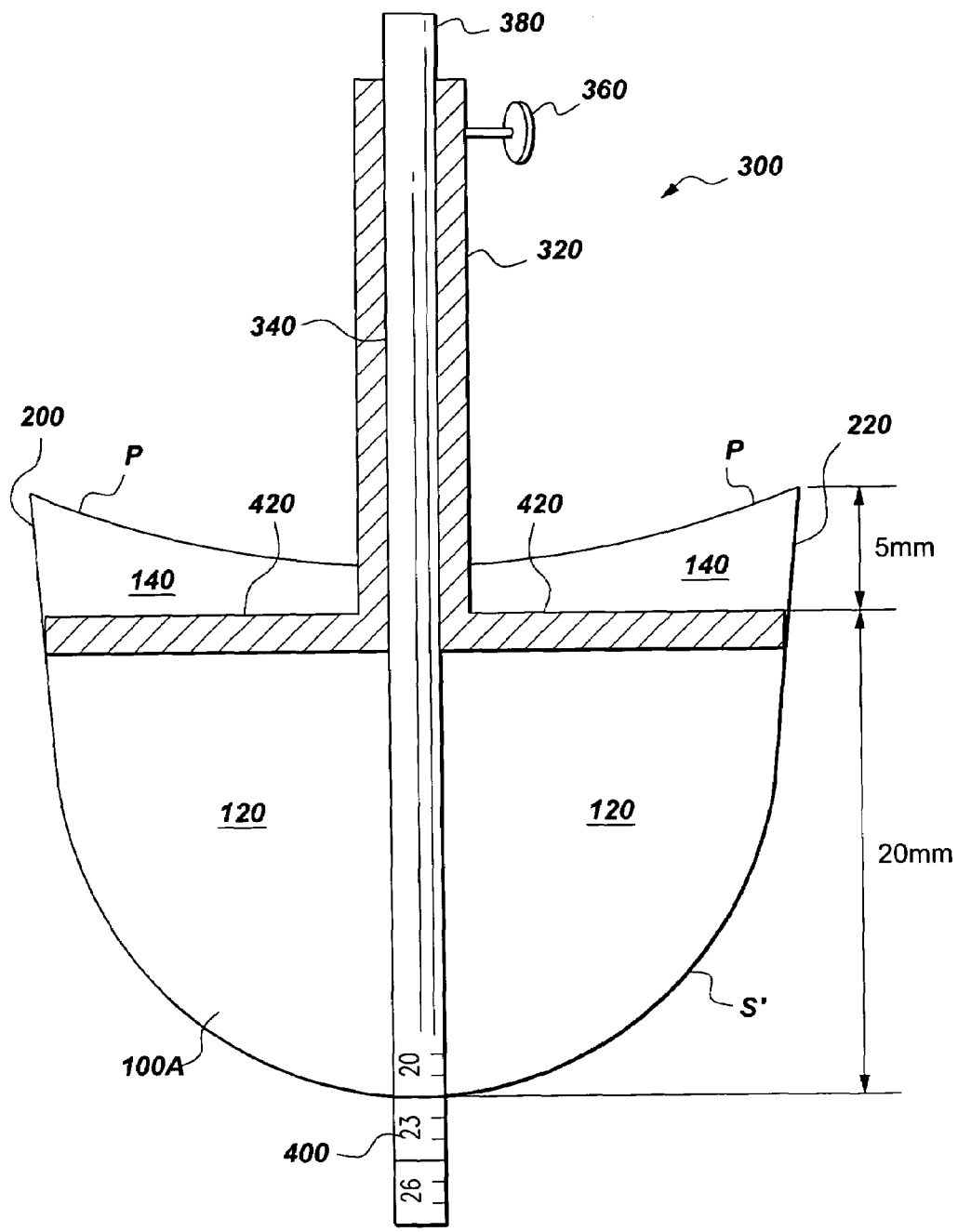
FIG. 16 shows a non-native leaflet-measuring device, according to the invention.
Figure 17:
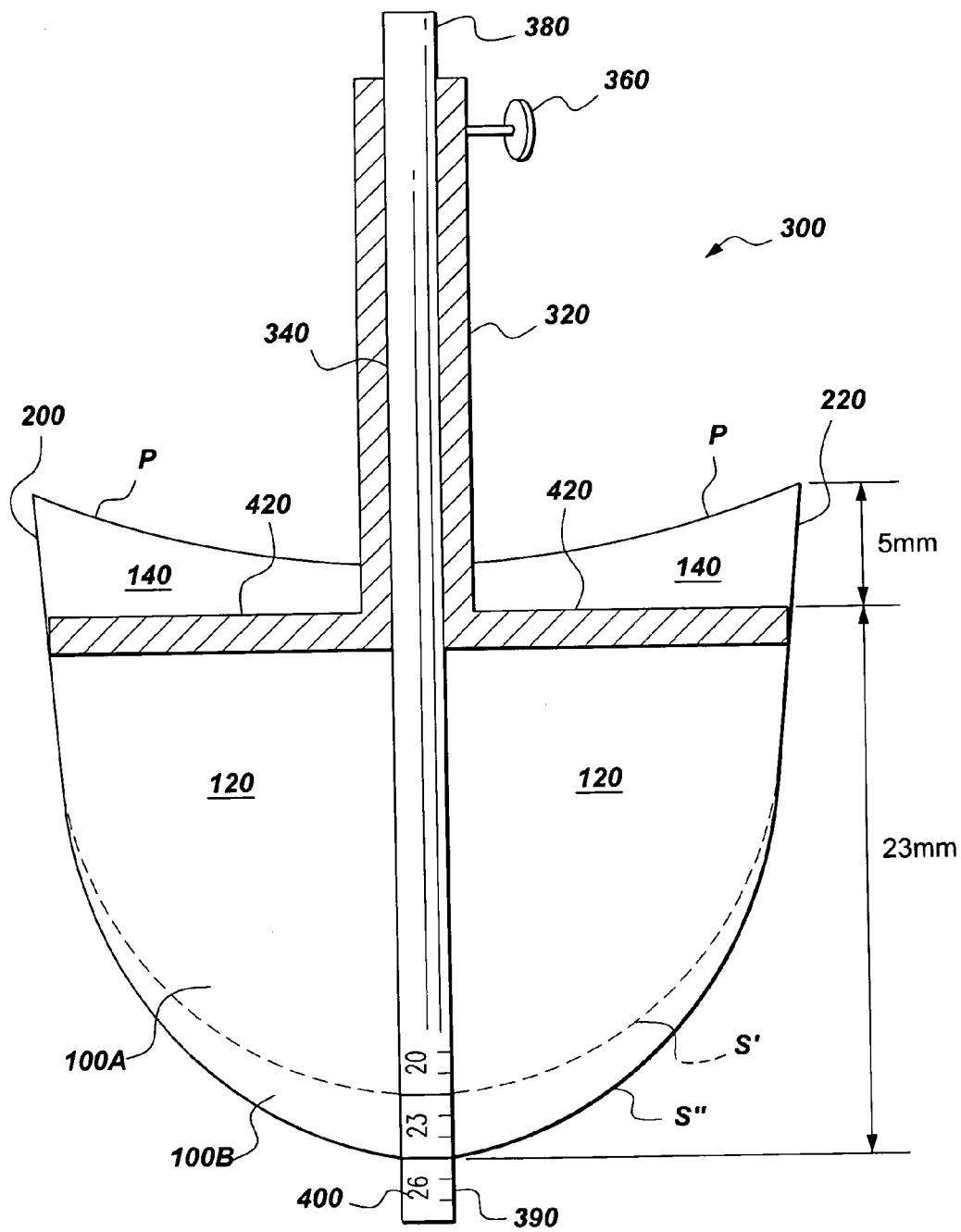
FIG. 17 shows a non-native leaflet-measuring device, according to the invention.
Figure 18:
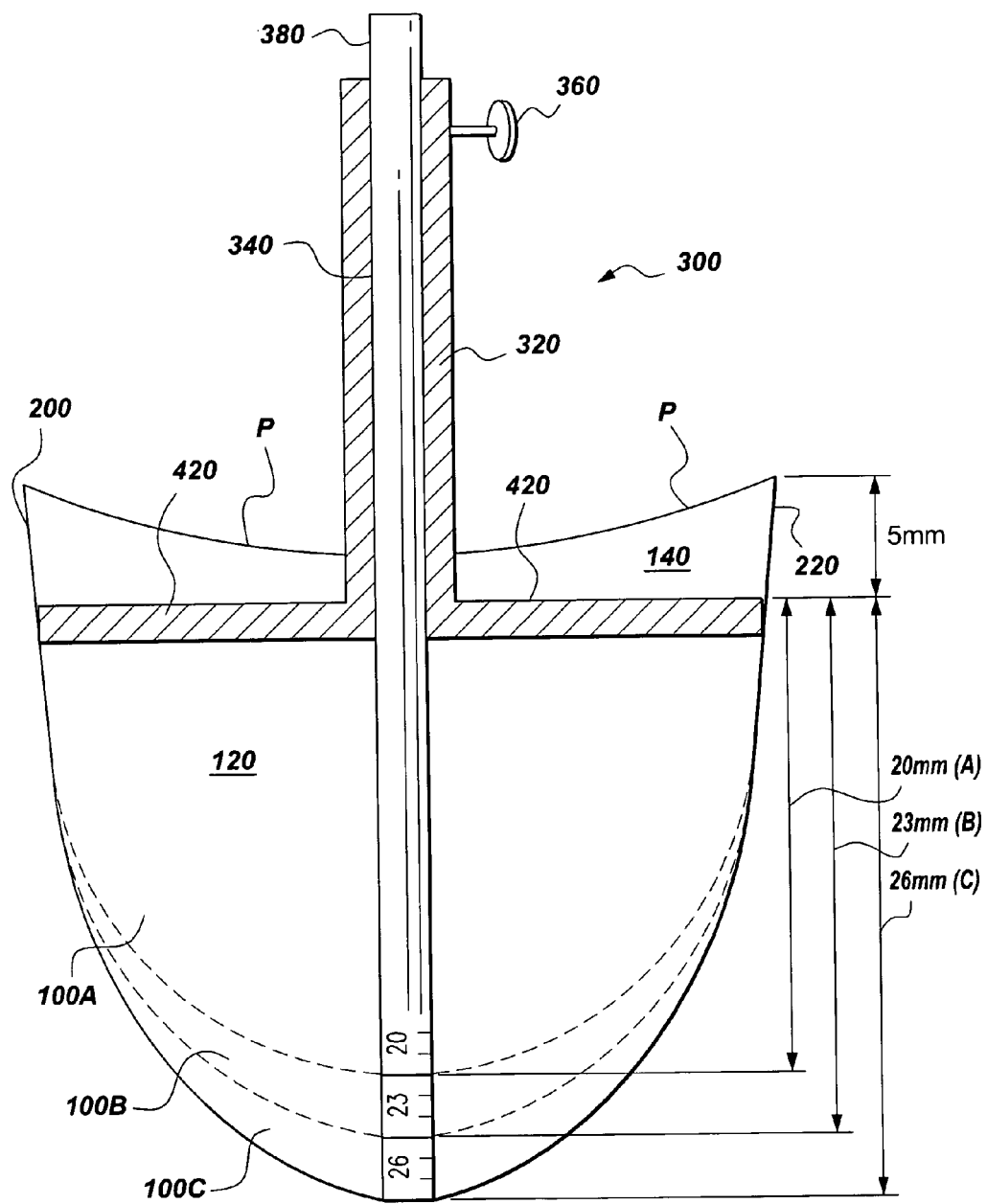
FIG. 18 shows a non-native leaflet-measuring device, according to the invention.
Figure 19:
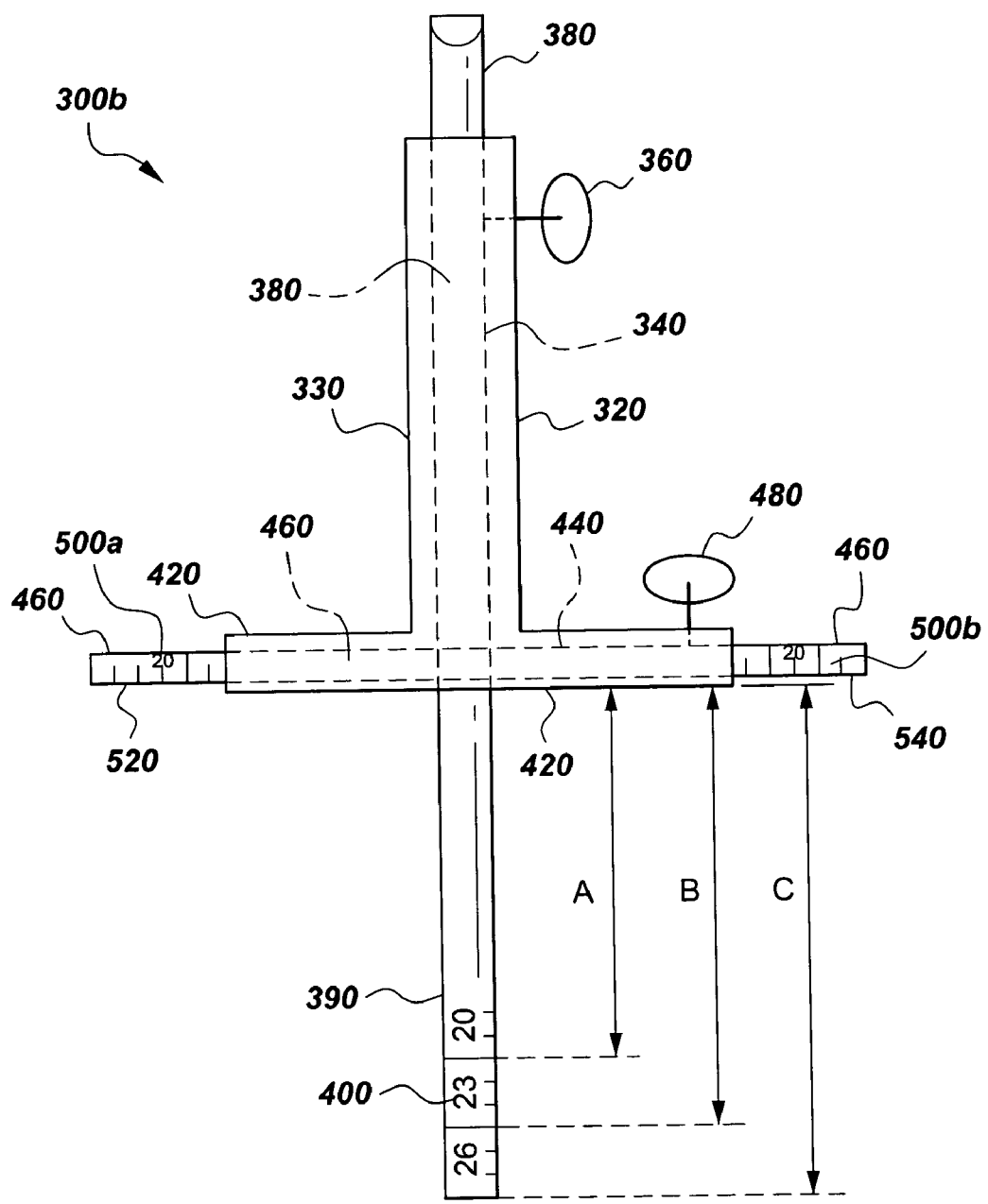
FIG. 19 shows a measuring device configured to take measurements of a patient's aortic valve to provide custom measurements for use in making non-native replacement aortic leaflets, according to the invention.
Figure 19A:
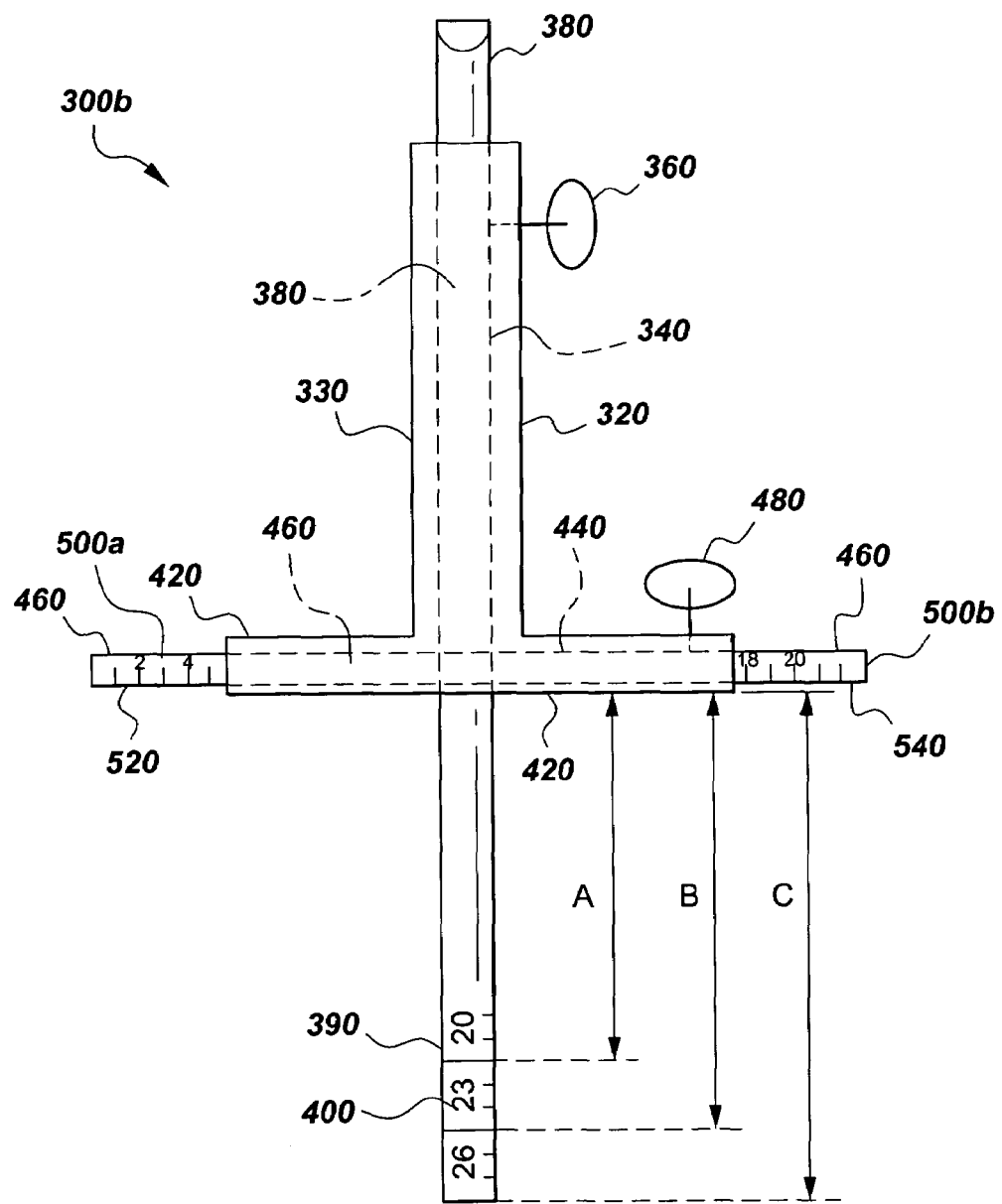
FIG. 19A shows a measuring device configured to take measurements of a patient's aortic valve to provide custom measurements for use in making non-native replacement aortic leaflets, according to the invention.
Figure 20:
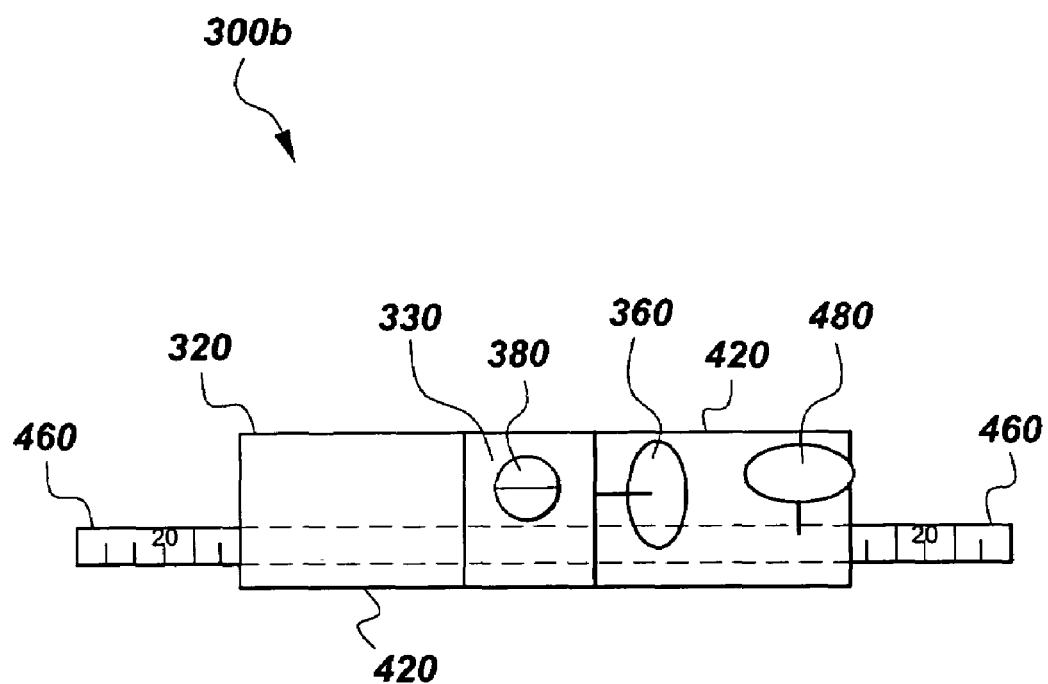
FIG. 20 shows a top end on view of the measuring device of FIG. 19.
Figure 21:
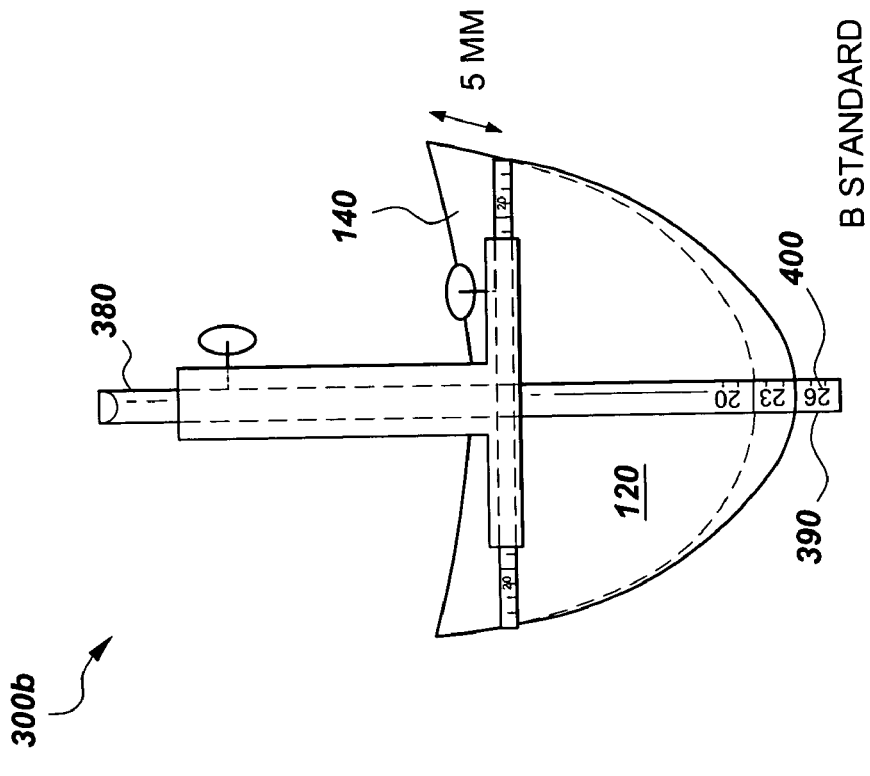
Figure 22:
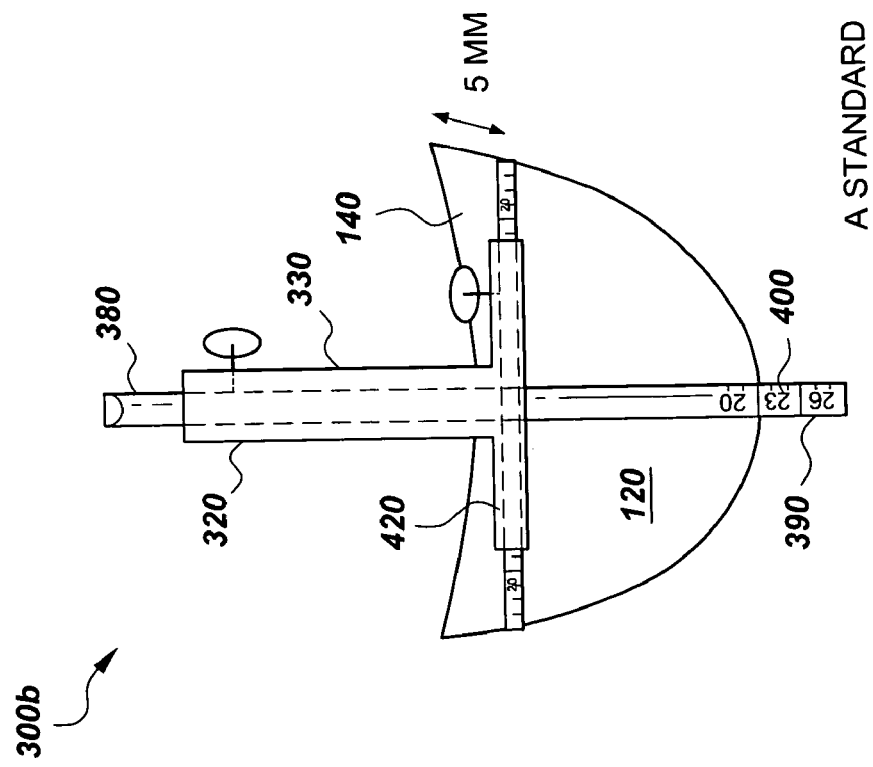

Sides 200 and 220 are shown as approximately parallel to each other, but sides 200 and 220 can diverge or converge with respect to each other. Front side 240 is shown as a concave curve with a minima M*. The area enclosed by perimeter P and virtual line L should be sufficient to allow the replacement leaflet 100 to function properly in cooperation with neighbor leaflets (native or non-native replacement leaflets 100 of the present invention) to enable proper functioning of the patient's aortic valve (as shown in FIGS. 9 and 10).

Still referring to FIGS. 2A, 2B and 2C, first and second peripheries S and P, and virtual line L all share the same opposite end points 160 and 180. Exemplary replacement leaflet 100 is shown having two-fold symmetry along longitudinal axis represented dashed line LS, wherein line LS travels through minima M*, midpoint M, and midpoint A. However, it will be understood that the shape mapped out, for example, first periphery S might vary from a perfect curve so that replacement leaflet 100 of the present invention does not always exhibit perfect two-fold symmetry, but will often exhibit approximate two-fold symmetry. For example, replacement leaflets 100', 100", and 100''' in FIG. 3C exhibit, at best, approximate two-fold symmetry.

It should be understood that the term "virtual triangle" refers to a virtual triangle generated by examining the aortic valve of a patient. More specifically, a virtual triangle T is derived, as described below (see, e.g., FIGS. 3A through 3E), from a suitable image of the aortic valve AV obtained using any suitable form of imaging technique (past, present or any suitable as yet undiscovered future imaging technique), such as, but not limited to: computed tomography (CT), magnetic resonance imaging such as cardiovascular magnetic resonance (CMR), ultrasonic echocardiography such as conventional 2-dimensional (2D) Doppler echocardiography or three-dimensional (3D) echocardiography or pulsed-wave Doppler tissue imaging (DTI, also sometimes referred to as tissue Doppler imaging (TDI)), Color M Mode echocardiography, alone or in combination.

Echocardiography images can be stored in electronic format or digital format on any suitable storage medium such as, but not limited to: USB flash memory drives, USB card disks, magnetic media (such as a computer hard drive or a removable disc such as a 3.5" floppy disc, magnetic tape), a laser readable DVD or CD such as a read/write CD (i.e., a CD-RW) or a compact disc-read-only memory (i.e., a CD-ROM).

Figure 3A:
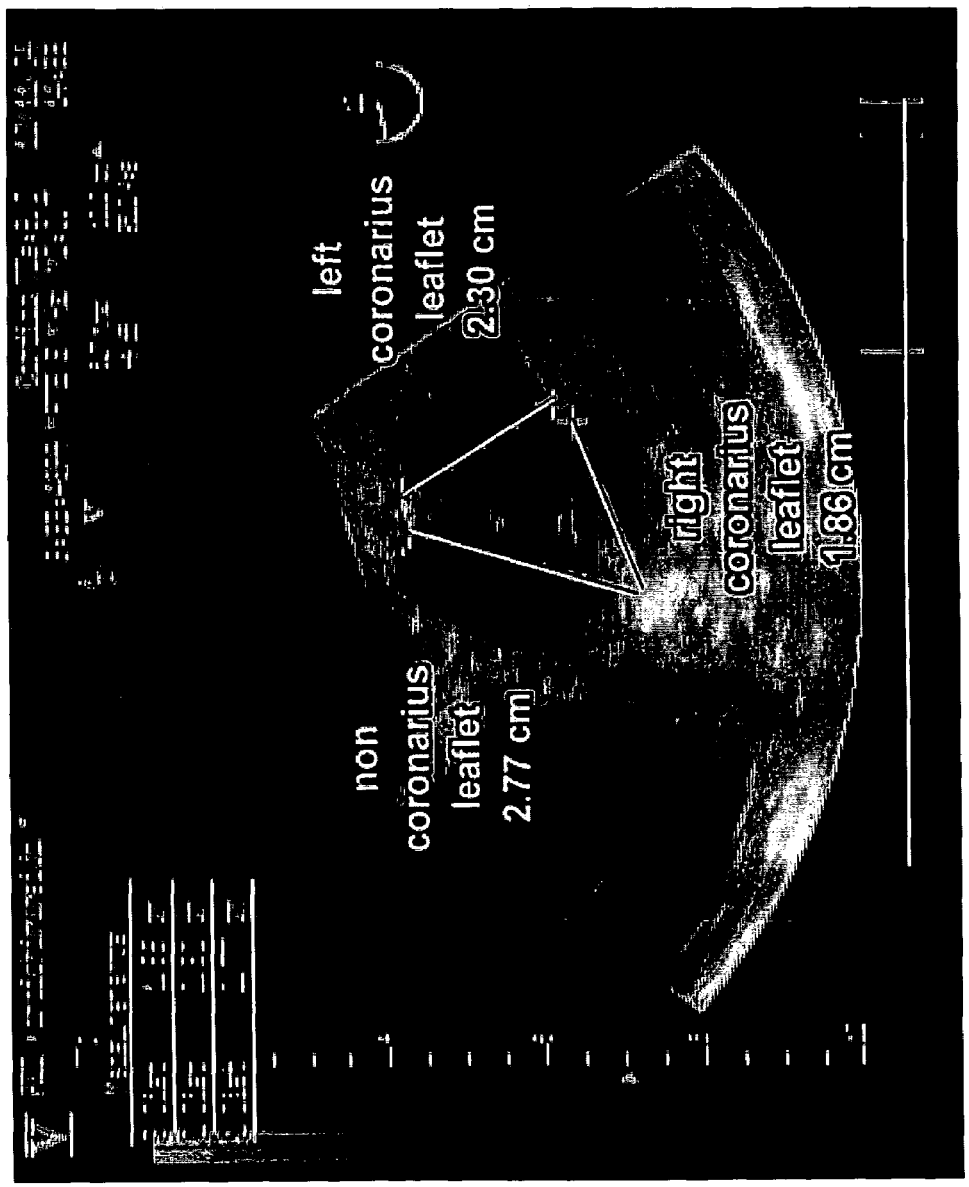
FIG. 3A shows an image of a patient's aortic valve obtained via echocardiography.
Figure 3B:
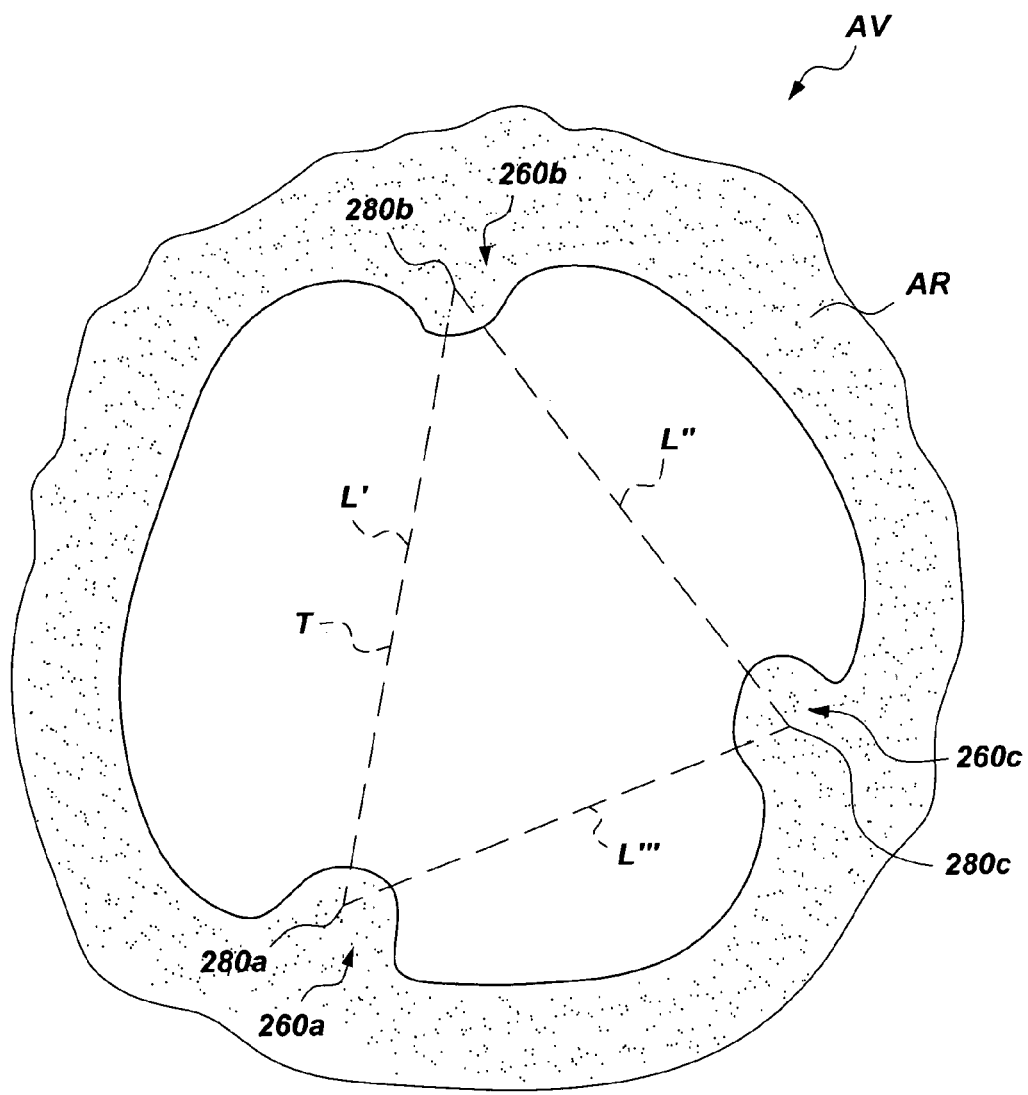
FIG. 3B is a schematic representation of the aortic valve of FIG. 3A with virtual lines L representing respective inter-commissure distances between selected aortic commissures, in this example, inter-commissure distances L', L", and L"' superimposed between first and second, second and third, third and first neighboring aortic commissures, such that the virtual lines L', L", and L"' form a virtual triangle T.

Referring to FIGS. 3A and 3B, FIG. 3A shows an image of a patient's aortic valve AV obtained using echocardiography, and FIG. 3B shows a schematic outline of the aortic valve AV of FIG. 3A. From the image shown in FIG. 3A, and correcting for any scaling issue, the actual distances between each pair of aortic commissures (three possible pair combinations) can be determined with respect to the first, second, and/or third replacement leaflets, 100', 100", and/or 100''', respectively.

Referring to FIG. 3B, virtual lines L', L", and L''' are shown superimposed over the aortic valve AV of FIG. 3A, such that the virtual lines L', L", and L''' form a virtual triangle T having first, second and third vertices 280a, 280b, and 280c, wherein the vertices 280a, 280b, and 280c are located over the commissures 260a, 260b, and 260c, respectively. More specifically, vertices 280a, 280b, and 280c define triangle T from which first 100', second 100", and/or third 100''' replacement leaflets are made (e.g., cut from GA treated pericardium tissue) based on the lengths of virtual lines L', L", and L'''. The virtual triangle T is most often a scalene triangle, but other forms of triangle are possible such as an isosceles or equilateral triangle.

In more detail, with respect to the electrocardiography derived image of a patient's aortic valve AV (FIG. 3A) and schematic (FIG. 3B), the distances between the aortic commissures of a patient were measured as 2.77 cm (with respect to the first 260a and second 260b commissures), 2.30 cm (with respect to the second 260b and third 260c commissures), and 1.86 cm (with respect to the third 260c and first 260a commissures) for the non-coronarius, left coronarius and right coronarius leaflets, respectively.

Figure 3C:
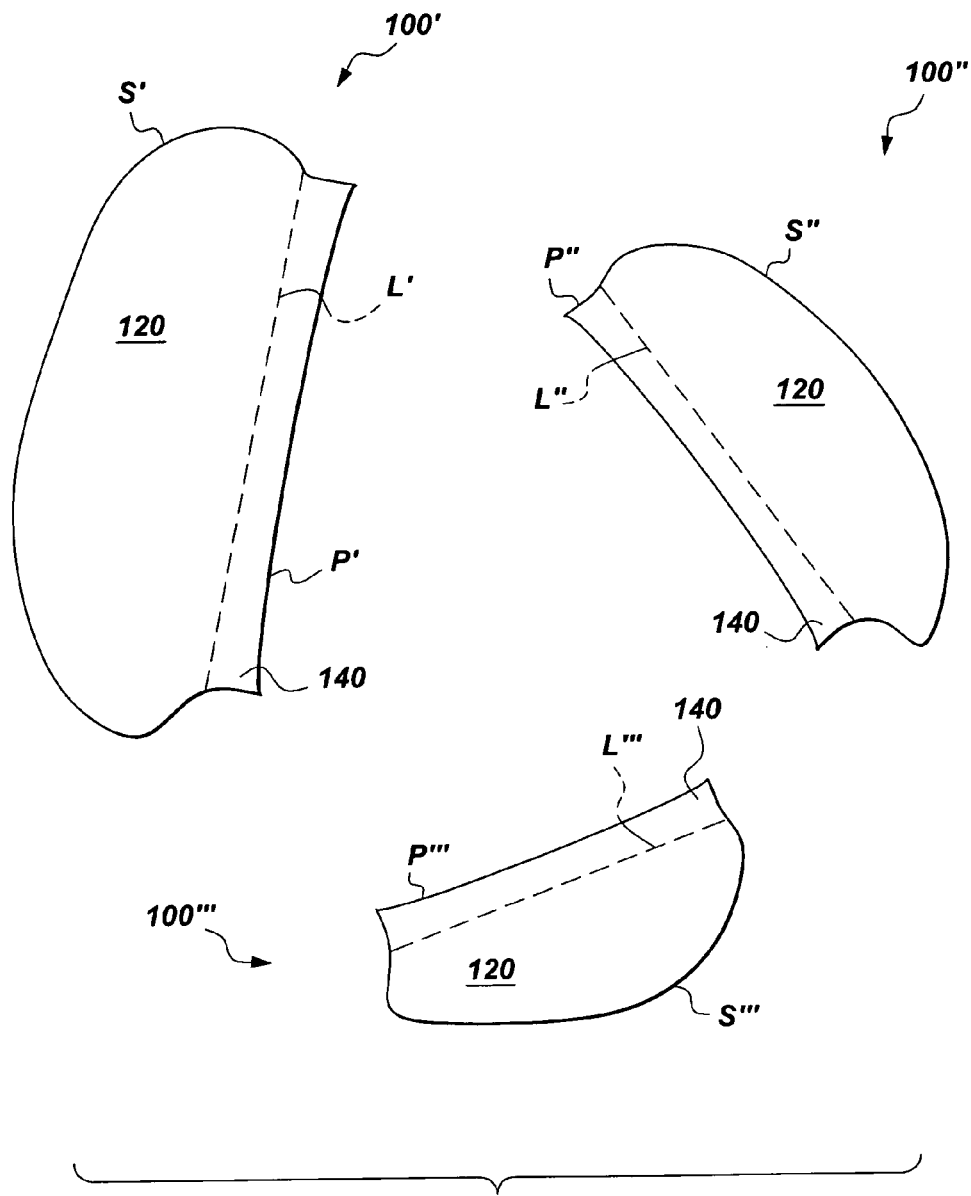
FIG. 3C shows three non-native leaflets according to the present invention based on L length data (i.e., L', L", and L"') derived from the electrocardiography image of FIG. 3A.

Referring to FIG. 3C, which shows three replacement leaflets 100', 100", and 100''' derived based on L length data derived from the echocardiography image of FIG. 3A. Specifically, if this patient required a non-coronarius leaflet, a replacement leaflet 100' would be fashioned out of suitable pericardium with a virtual line L having a length of about 2.77 cm (e.g., 2.8 cm). Likewise, if this patient required a left-coronarius leaflet, a replacement leaflet 100" would be fashioned out of suitable pericardium with a virtual line L" having a length of about 2.30 cm (e.g., 2.3 cm). Similarly, if this patient required a right coronarius leaflet, a replacement leaflet 100''' would be fashioned out of suitable pericardium with a virtual line L''' having a length of about 1.86 cm (e.g., 1.9 cm).

Figure 3D:
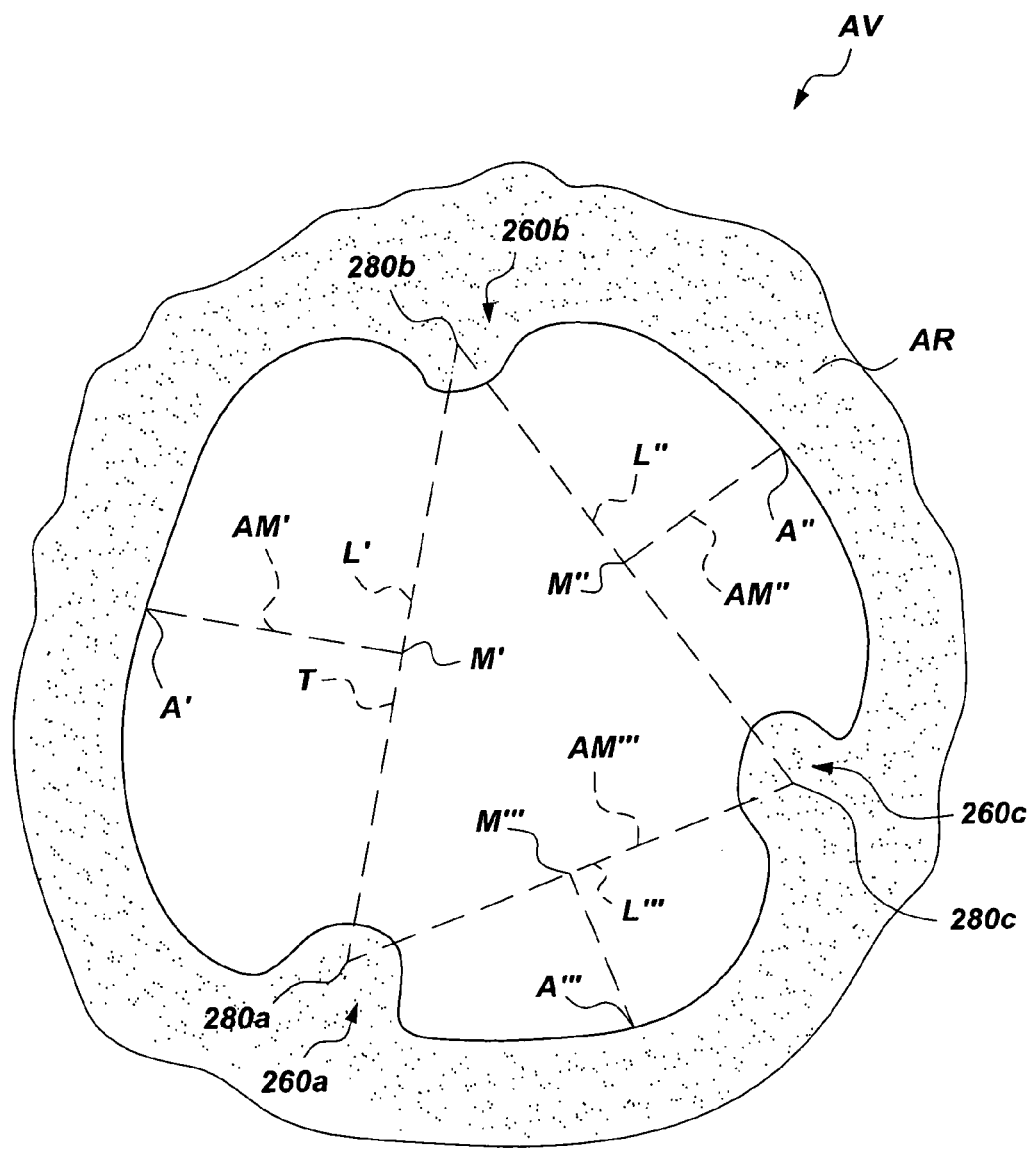
FIG. 3D is a further schematic representation of the aortic valve of FIG. 3A with virtual lines L', L", and L"' with virtual lines AM', AM", and AM"' superimposed over aortic valve AV of FIG. 3A.

Referring to FIG. 3D, virtual lines L', L", and L''' along with virtual lines AM', AM", and AM''' are shown superimposed over aortic valve AV, such that the virtual lines L', L", and L''' form a virtual triangle T having first, second and third vertices 280a, 280b, and 280c, wherein the vertices 280a, 280b, and 280c are located over the commissures 260a, 260b, and 260c, respectively. For example, the length dimension AM' is determined by extending a virtual perpendicular line from midpoint M' on virtual line L' until it intercepts the aortic ring between first and second commissures 260a and 260b and then measuring this line (referenced as "AM'"). Similarly, the length dimension AM" is determined by extending a virtual perpendicular line from midpoint M" on virtual line L" until it intercepts the aortic ring between second and third commissures 260b and 260c and then measuring this line (referenced as "AM'"). Similarly, the length dimension AM''' is determined by extending a virtual perpendicular line from midpoint M''' on virtual line L''' until it intercepts the aortic ring between third and first commissures 260c and 260a and then measuring this line (referenced as "AM''"").

Figure 3E:
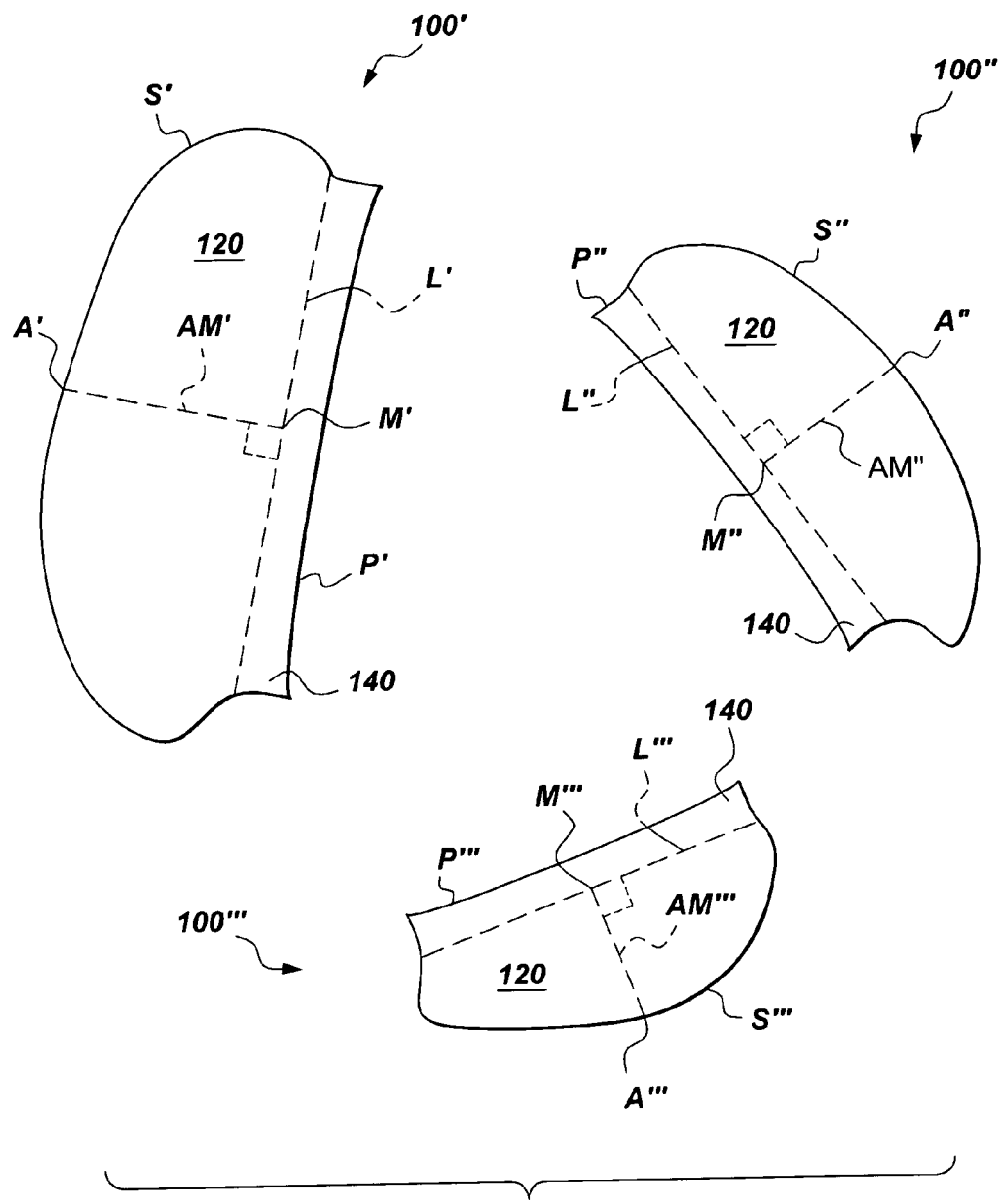
FIG. 3E shows three non-native leaflets according to the present invention based on L length data (i.e., L', L", and L"') and AM length data (i.e., AM', AM", and AM"') derived from the electrocardiography image of FIG. 3A. The terms "length dimension AM" and "depth dimension AM" are hereinafter regarded as equivalent terms.

FIG. 3E shows three replacement leaflets 100', 100", and 100''' derived based on L and AM length data derived from the electrocardiography schematic FIG. 3D. It will be understood that pericardium tissue such as GA treated equine pericardium, can be hand-stretched by a competent heart surgeon without causing significant loss of strength or increased risk of tears.

Figure 4A:
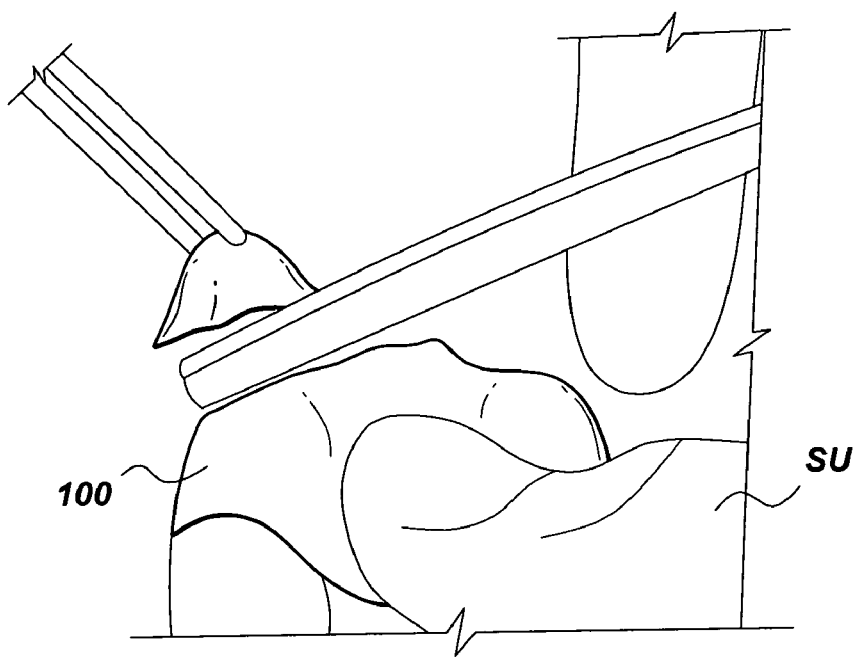
FIG. 4A shows a surgeon trimming a strip of pericardium to provide a non-native leaflet, according to the present invention.
Figure 4B:
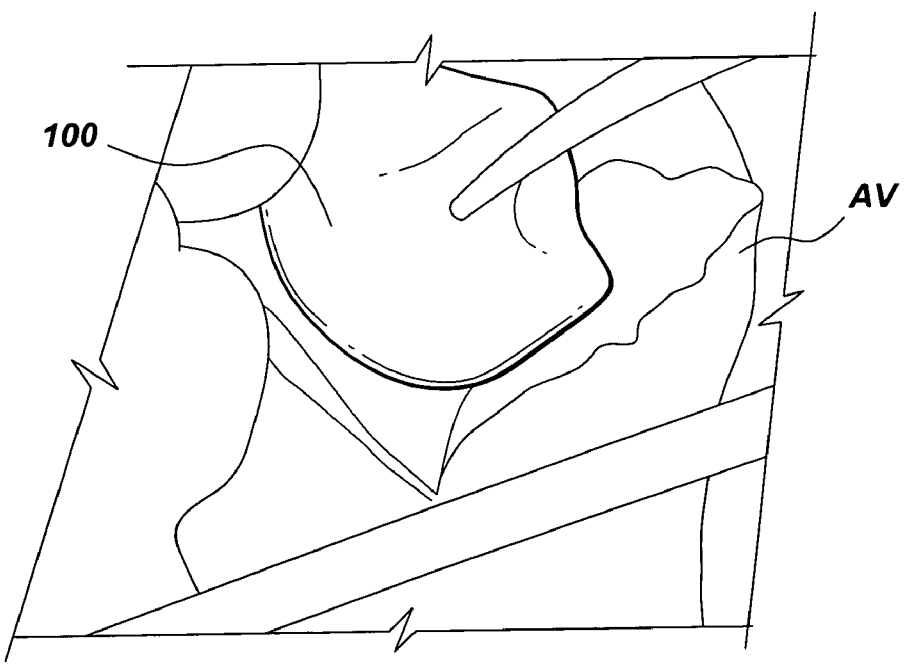
FIG. 4B shows a surgeon manipulating a non-native leaflet, according to the present invention.
Figure 5:
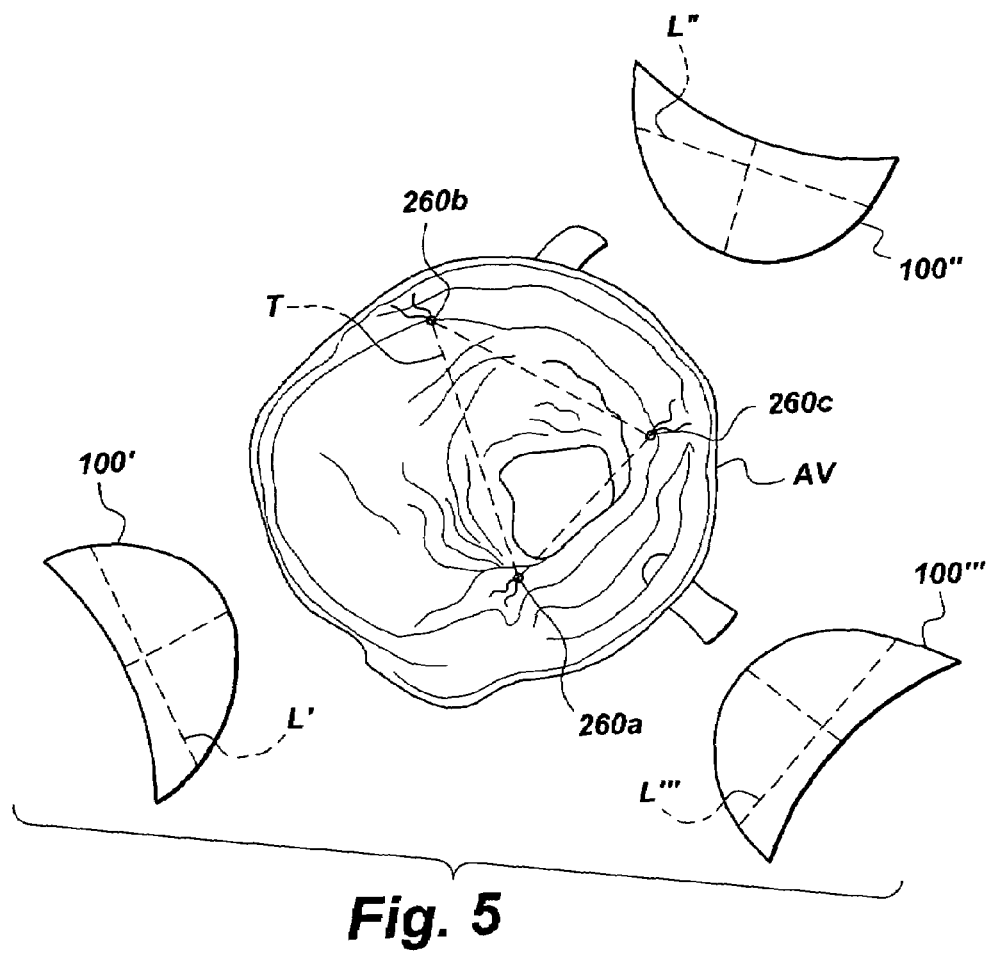
FIG. 5 shows three non-native leaflets about to be sutured to a patient's aortic valve, according to the present invention.
Figure 6:
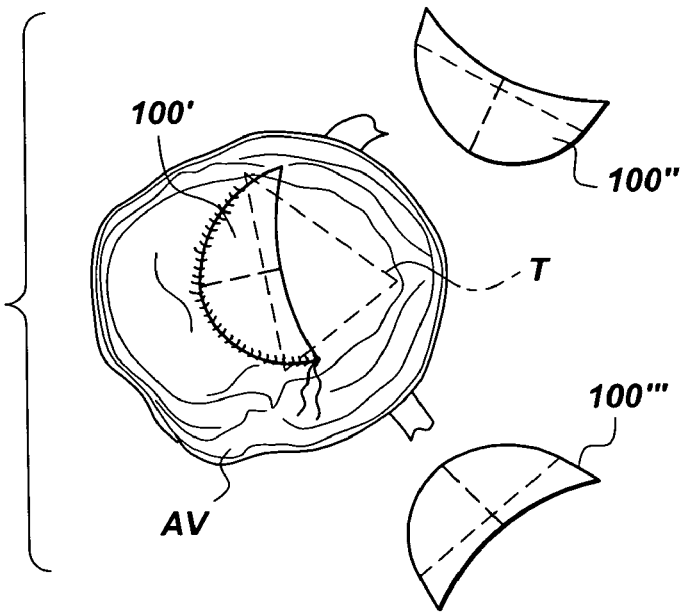
FIG. 6 shows a step in attaching the non-native leaflets of FIG. 5 to a patient's aortic ring.
Figure 7:
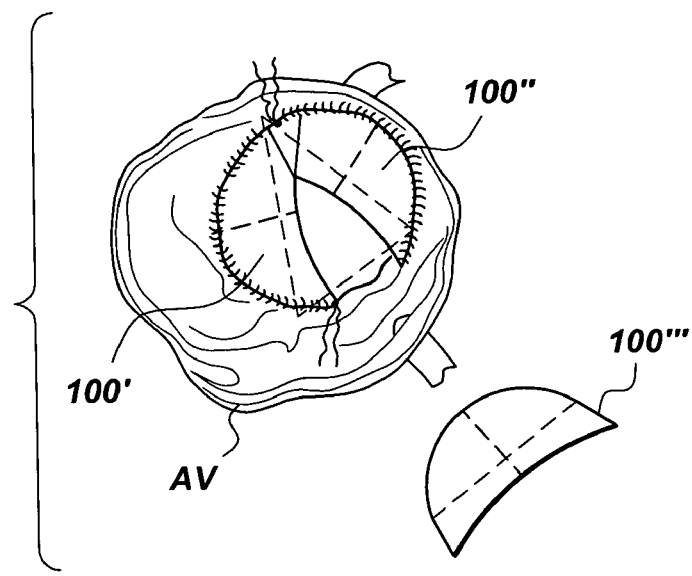
FIG. 7 shows a further step in attaching the non-native leaflets of FIG. 5 to a patient's aortic ring.
Figure 8:
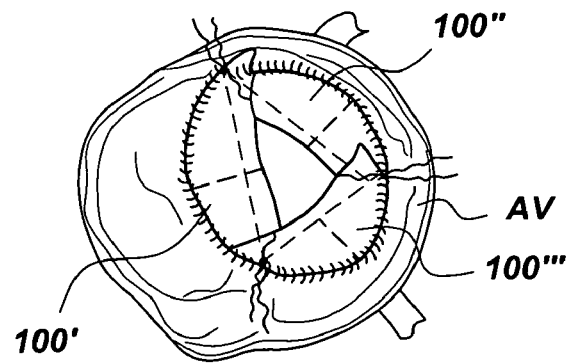
FIG. 8 shows a further step in attaching the non-native leaflets of FIG. 5 to a patient's aortic ring.

It will be understood that a skilled heart surgeon can take a strip of pericardium tissue and cut it into a second strip of having a width corresponding to inter-commissural dimension L, and while operating on a patient's aortic valve AV, trim and manipulate the strip to provide a desired shape for replacement leaflet 100. For example, FIGS. 4A and 4B show a surgeon Su trimming and otherwise manipulating a strip of pericardium to provide a replacement leaflet 100. Thus, while the actual value of AM is desired, knowledge of the actual value of AM is not required by the heart surgeon to replace one or more diseased or damaged aortic leaflets.

FIGS. 5 through 8 show how a surgeon (not shown) can shape leaflets replacement 100a, 100b, and 100c and attach each leaflet in turn by suturing each replacement leaflet to at least one aortic commissure and further attaching each leaflet by means of suturing first periphery S of each leaflet to appropriate sections of aortic ring AR as shown.

FIGS. 9 and 10 show an aortic valve AV in a patient that has received three replacement leaflets 100', 100'', and 100''' attached as described by FIGS. 5 through 8. It will be understood that one, two or three native diseased or damaged leaflets can be replaced with replacement leaflets 100 of the present invention.

FIGS. 11 through 14 show how a surgeon (not shown) can attach each leaflet in turn by suturing each leaflet to at least one aortic commissure and further attaching the first periphery S of each leaflet to appropriate sections of aortic ring AR between selected pairs of commissures, using a stapler device SD.

As described above, the shape and dimensions of each replacement leaflet 100 is predetermined based on L, or a combination of L and AM values, predetermined by any suitable imaging means such as echocardiography or otherwise determined at some point prior to the final cutting and trimming of the replacement leaflet 100. Alternatively, a standard set of numeric length values can be picked for inter-commissural dimension L and distance AM of replacement leaflet 100. For example, leaflets can be cut and trimmed with eight specific inter-commissural dimensions for L: 17 mm, 19 mm, 21 mm, 23 mm, 25 mm, 27 mm, 29 mm, 31 mm, 33 mm and 35 mm; i.e., 17 mm, 19 mm, 21 mm, 23 mm, 25 mm, 27 mm, 29 mm, 31 mm, 33 mm and 35 mm represent typical distances from commissure to commissure. Combining these numeric values for inter-commissural dimension L with three lengths for AM will produce 30 possible leaflets.

A non-native leaflet-measuring device 300 for measuring inter-commissural dimensions L and parameter AM in non-native replacement leaflets 100 of the present invention is shown in FIGS. 15 through 18. The measuring device 300 comprises a T-shaped member 320 having a hollow vertical bore 340. The T-shaped member 320 is shown in partial cross-section. Device 300 further includes a first fixator member 360, and a first shaft 380. First shaft 380 is housed in bore 340 and is used to measure distance AM associated with segment 120. First shaft 380 is optionally removable from bore 340 thereby allowing a substitute or replacement shaft to be inserted into bore 340. Numeric measurement indicia 400 are etched or presented on the lower end 390 of shaft 380. Alternatively, first shaft 380 may be fixed permanently inside bore 340 of T-member 360. T-shaped member 320 further includes a horizontal arm 420. The horizontal arm 420 is used for measuring inter-commissural dimension L.

First shaft 380, and in particular the lower end 390 of first shaft 380, is used for AM measurements. With respect to FIG. 15, an AM length of 20 mm is classified as "type A"; an AM length of 23 mm is classified as "type B"; and an AM length of 26 mm is classified as "type C". Combining these AM classifications with different values for the inter-commissural dimension L enables different replacement leaflets 100 (represented by alpha-numeric labels "100A", "100B", and "100C") with specific segment 120 dimensions to be made and stored for later use using a suitable storage medium and temperature. It will be immediately understood by a person of ordinary skill in the art that a variety of measuring devices 300 can be provided each having a horizontal arm 420 of slightly different length corresponding to a predetermined length value for the inter-commissural dimension L. For example, six length values for inter-commissural dimension L, combined with AM types A, B, and C (see FIG. 15) will provide twenty-four possible leaflets.

In one aspect of the present invention, a method of fashioning a plurality of standardized replacement aortic leaflets 100 is provided, and comprises the step of: fashioning a plurality of non-native replacement leaflets 100, wherein each of the replacement leaflets comprises first and second segments 120 and 140, separated by a virtual line L having a predetermined length, wherein the first 120 and second 140 segments of each replacement leaflet 100 are respectively bounded by first and second peripheries S and P, wherein the first and second peripheries S and P and the virtual line L share the same first and second opposite ends, wherein the virtual line L defines a midpoint M, wherein the first periphery S defines a first periphery midpoint A, wherein each replacement leaflet 100 incorporates a length dimension AM, wherein AM is defined by a virtual perpendicular line that extends from the midpoint M on virtual line L to the midpoint A of the first periphery S, and wherein the plurality of replacement leaflets 100 comprises leaflets with predetermined values for L and AM. It will be understood that midpoint A on first periphery S is merely the intercept point between virtual perpendicular line AM and periphery S.

For example, a standard set of leaflets can be provided by cutting and trimming leaflets to correspond to eight specific inter-commissural dimensions for L: 17 mm, 19 mm, 21 mm, 23 mm, 25 mm, 27 mm, 29 mm, 31 mm, 33 mm and 35 mm; i.e., 17 mm, 19 mm, 21 mm, 23 mm, 25 mm, 27 mm, 29 mm, 31 mm, 33 mm and 35 mm represent typical distances from commissure to commissure. Combining these numeric values for inter-commissural dimension L with, for example, three lengths for AM such as 20 mm, 23 mm, and 26 mm will produce 30 different sized leaflets 100, each of the 30 different sized leaflets comprising glutaraldehyde treated pericardium. Thus, a heart surgeon can select one or more leaflets from a standard set of leaflets to replace one or more defective aortic valve leaflets in a patient requiring such treatment. The standard set of leaflets can have several copies of each standard leaflet provided in the standard leaflet set.

Referring to FIGS. 19 through 25B, which show a measuring device 300b. The measuring device 300b can be used to check or measure the dimensions L and AM with respect to prospective replacement leaflets 100 (see, e.g., FIGS. 21 through 24). Alternatively, measuring device 300b can be used to measure lengths L and AM of a selected native aortic valve leaflet in a surgically opened aortic valve (see, e.g., FIGS. 25A and 25B). For example, measuring device 300b enables a heart surgeon Su to obtain one or more inter-commissure distances (e.g., L', L'', and/or L''') and/or AM, e.g., AM', AM'', and AM''') to fashion non-native pericardium into one or more replacement aortic valves 100 for suturing or stapling directly into a patient's diseased aortic valve DAV.

Still referring to FIGS. 19A through 25B, the measuring device 300b comprises a T-shaped member 320 having a vertical arm 330, first bore 340, first fixator member 360, first shaft 380, and a horizontal arm 420. First fixator member 360 is used to hold first shaft 380 in place. First shaft 380 is housed in first bore 340.

Still referring to FIGS. 19 through 25B, the horizontal arm 420 has a second hollow bore 440. Second hollow bore 440 houses a one-piece second shaft 460 for measuring inter-commissural dimensions L. A second fixator member 480 is used to hold second shaft 460 in place inside second hollow bore 440. Numeric measurement indicia 400 are etched or otherwise disposed on the lower end 390 of shaft 380. Additional numeric measurement indicia 500a and 500b are etched or otherwise respectively disposed at opposite ends 520 and 540 of second shaft 460.

In one embodiment, the shafts 380 and 460 of device 300b can be removed and/or replaced. In this embodiment, the measuring device 300b or its component parts can be sterilized alone or in combination. For example, shafts 380 and 460, T-shaped member 320, and first and second fixators 360 and 480 can be sterilized alone or in combination. The component parts of device 380 can be made of any suitable material such as, but not limited to, metal or plastic amenable to at least one known sterilization technique such as heat treatment (e.g. steam sterilization/autoclaving), chemical/gas sterilization (e.g., ethylene oxide treatment), or radiation sterilization (e.g., by exposure to gamma-rays).

Figure 25A:
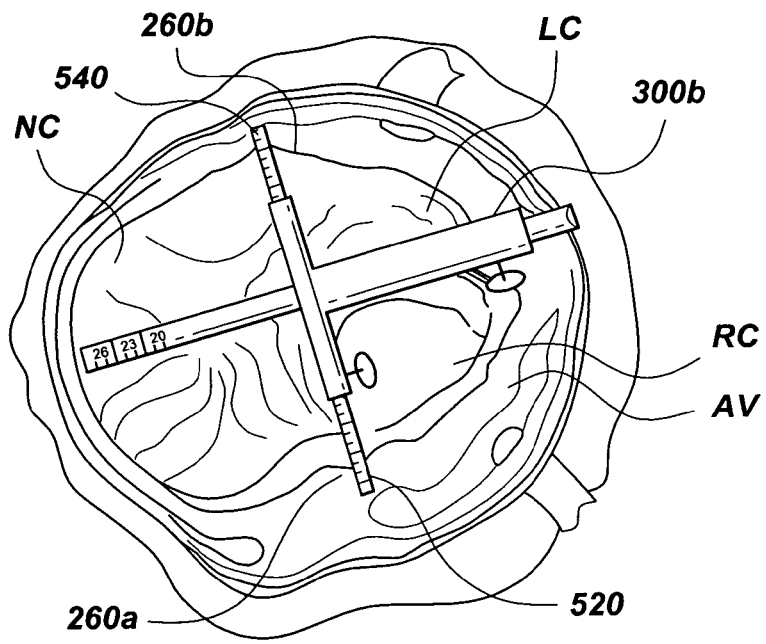
FIGS. 25A and 25B show how the measuring device of FIG. 19 is used to measure lengths L and AM of a selected aortic valve leaflet in a surgically opened aortic valve.
Figure 25B:
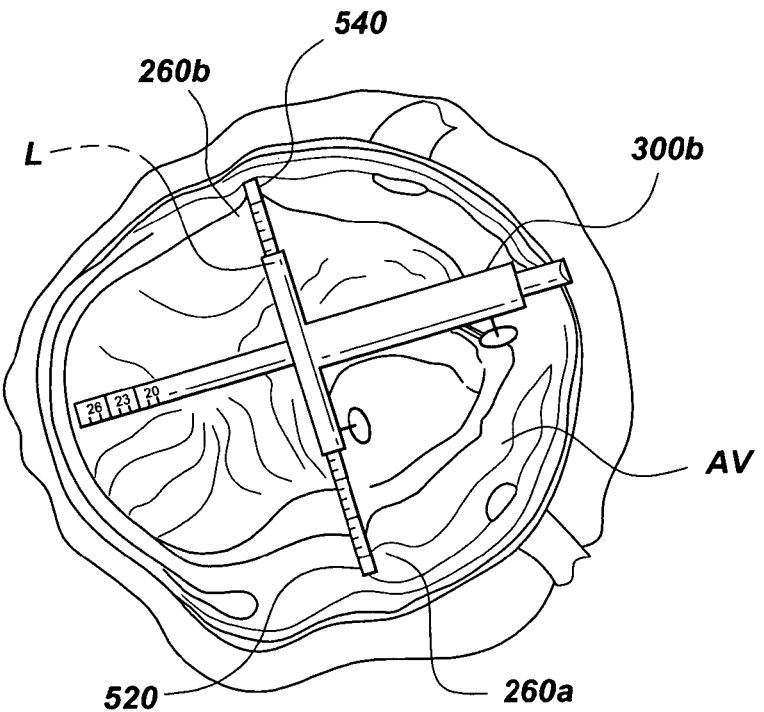

The measuring device 300b can be used to directly measure the inter-commissure distance L between two selected aortic commissures, such as 260a and 260b (see FIG. 3B), by placing opposite shaft ends 520 and 540 over two selected aortic commissures 260a and 260b and reading off the distance L between the two selected aortic commissures. Specifically, a surgeon SU need not exactly align one or both shaft ends 520 and/or 540 with either of the selected aortic commissures 260a and/or 260b. FIGS. 25A and/or 25B show an exemplary non-limiting example of how this simple procedure is achieved: (i) the opposite ends 520 and 540 are placed over two selected aortic commissures 260a and 260b; (ii) first and second measurements are taken (e.g., 22 mm and 20 mm with respect to opposite shaft ends 520 and 540); and (iii) the first and second measurements are summed and then divided by two to provide the inter-commissure distance L of 21 mm.

Figure 26A:
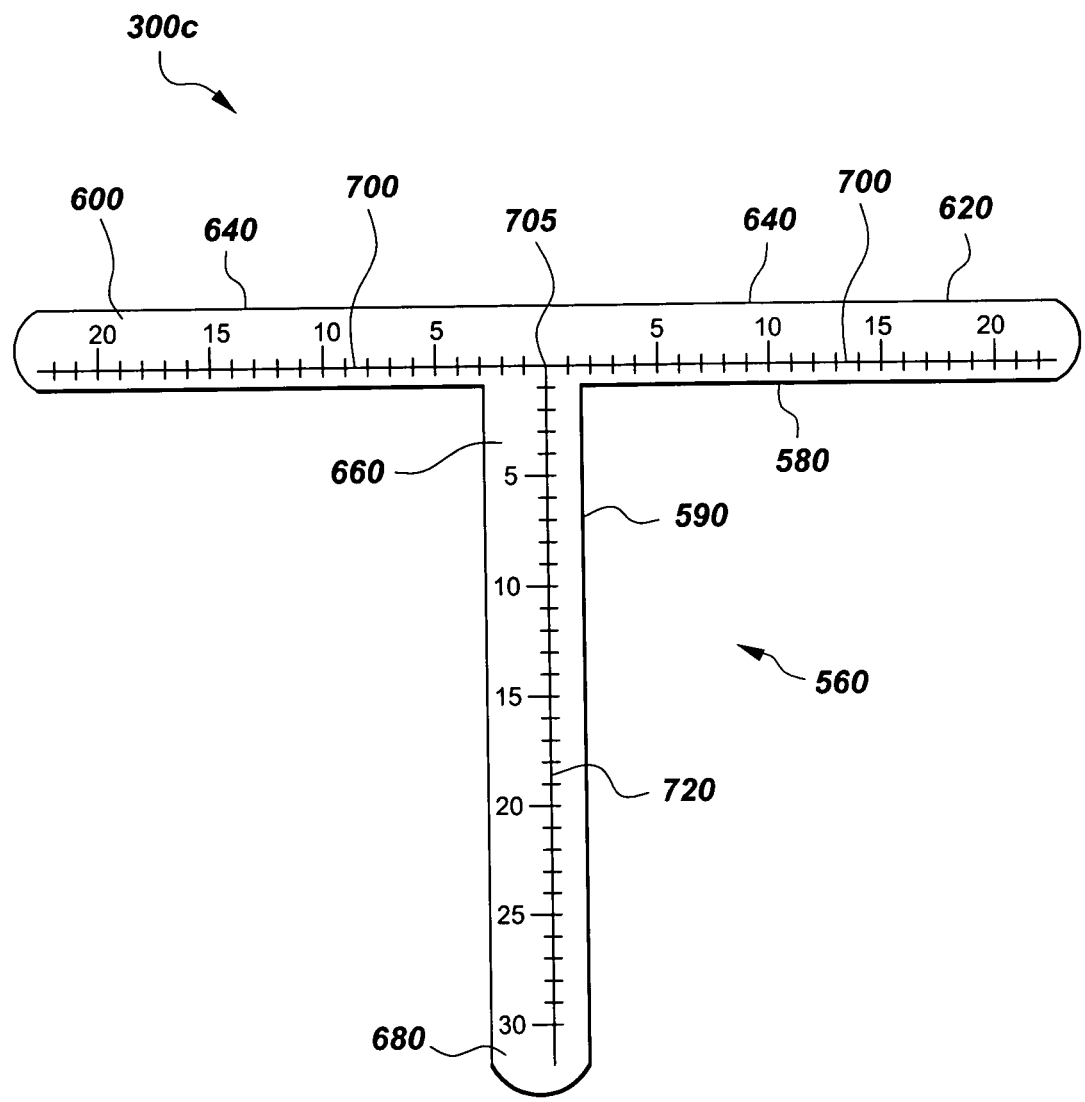
FIG. 26A shows a further measuring device for measuring dimensions L and AM.

FIG. 26A shows a still further embodiment of the measuring device 300, represented by alpha-numeral label "300c". Measuring device 300c is a generally T-shaped member 560 comprising an L distance measuring member 580, and an AM measuring member 590. The L distance-measuring member 580 has first 600 and second 620 opposite ends and a middle section 640 between the first 600 and second 620 opposite ends. The AM measuring member 590 has first 660 and second 680 opposite ends. The first end 660 of the AM measuring member 590 is connected to the middle section 640 of the L distance-measuring member 580 thereby defining the T-shaped member 560. Indicia 700 on member 580 counts up in a left and right direction about midpoint 705. The measuring device 300c can be made out of any suitable material such as transparent plastic capable of sterilization by, for example, gamma rays.

Figure 26B:
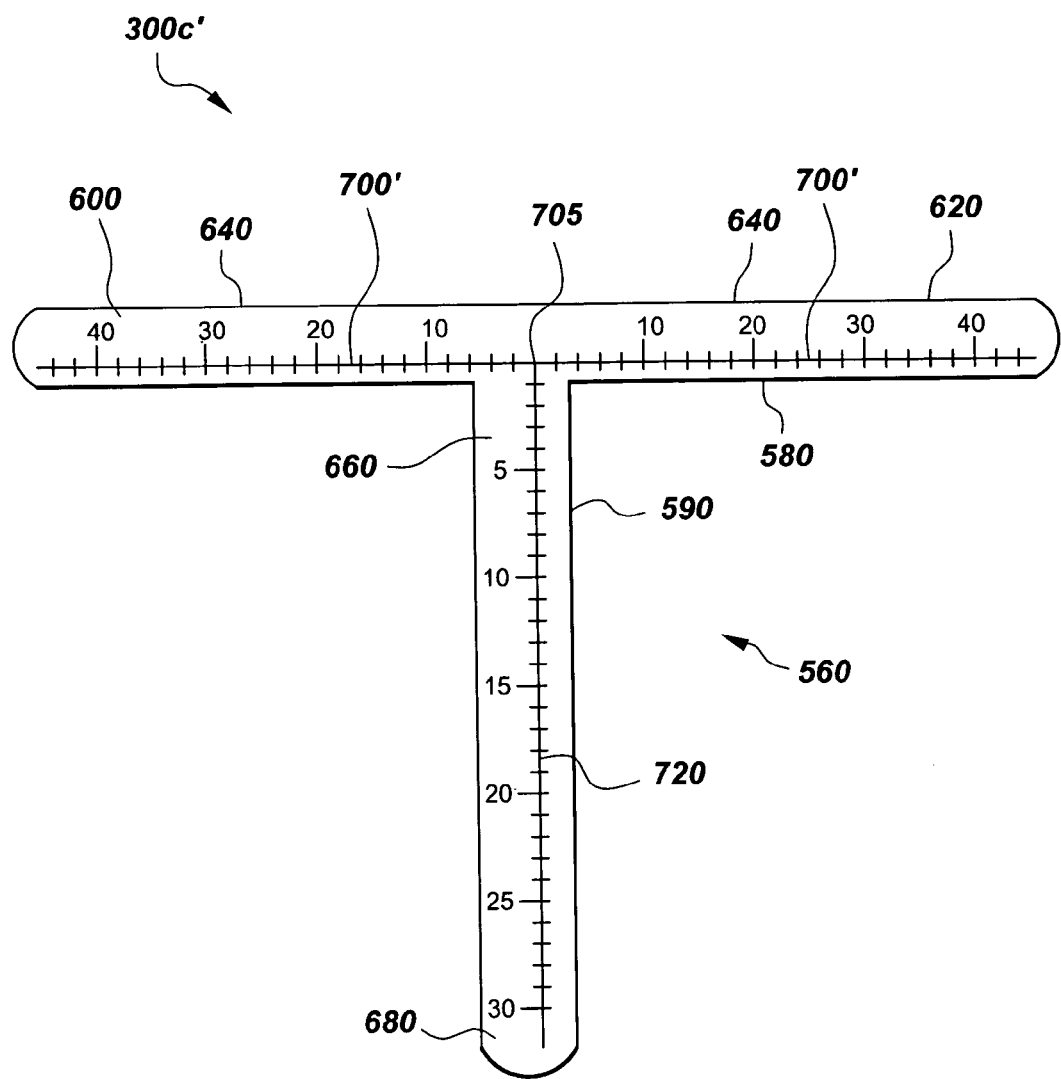
FIG. 26B is a variation on the measuring device of FIG. 26A.

FIG. 26B shows a variation of device 300c (represented by alpha-numeric label "300c'") in which indicia 700' on member 580 counts up linearly in multiples of 2 from midpoint 705.

Still referring to device 300c, the dimensions of the L distance-measuring member 580 can vary, but is generally less than about 40 mm in length, and more preferably less than about 30 mm in length and still more preferably about 25 mm in length. Numeric measurement indicia 700 are located along member 580. The dimensions of the AM measuring member 590 can vary, but is generally less than about 40 mm in length, and more preferably less than about 30 mm in length and still more preferably about 25 mm in length.

Numeric measurement indicia 720 are located at the second end 680 of the AM measuring member 590.

Figure 27A:
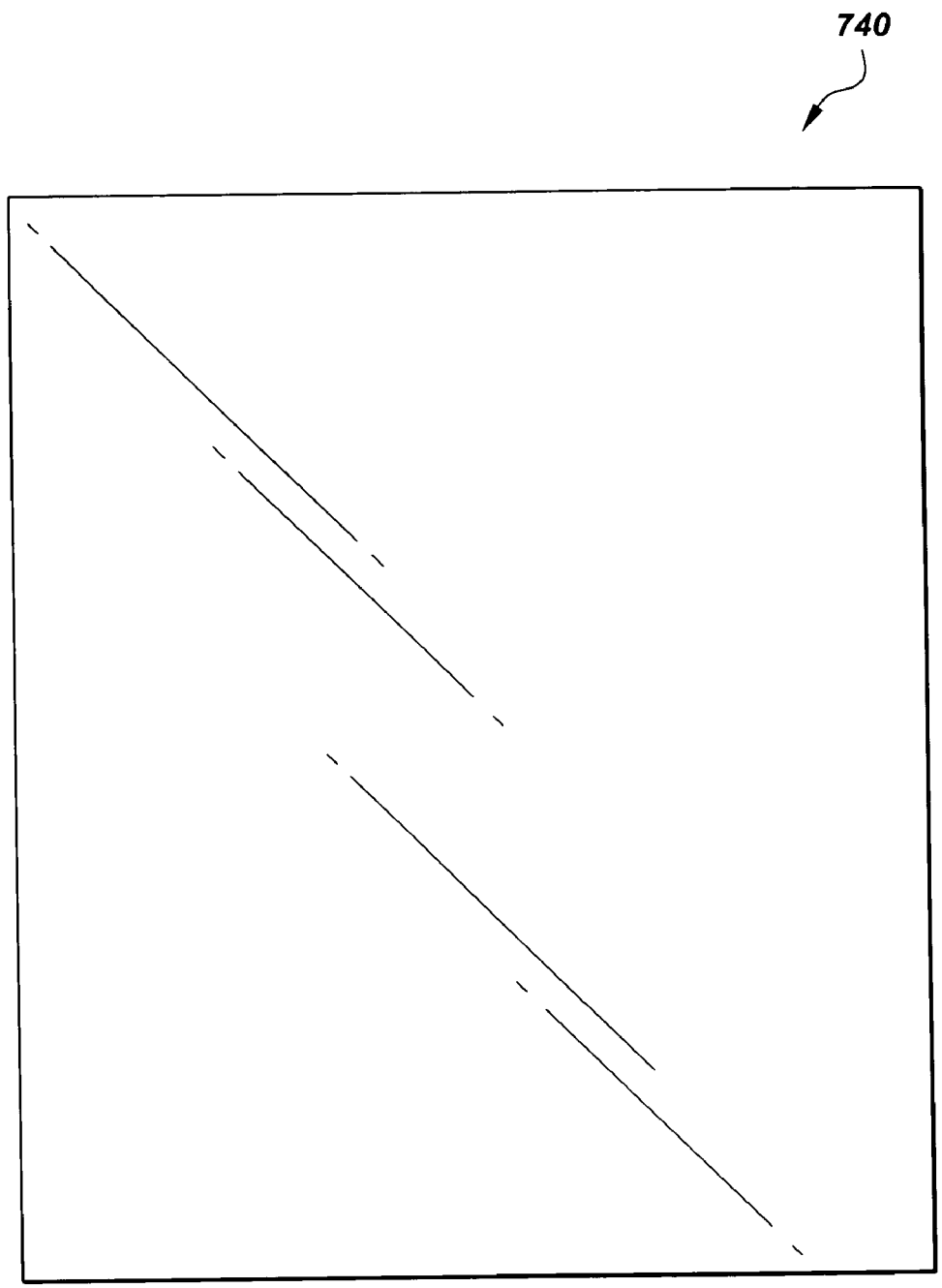
FIG. 27A shows a transparent sheet.
Figure 27B:
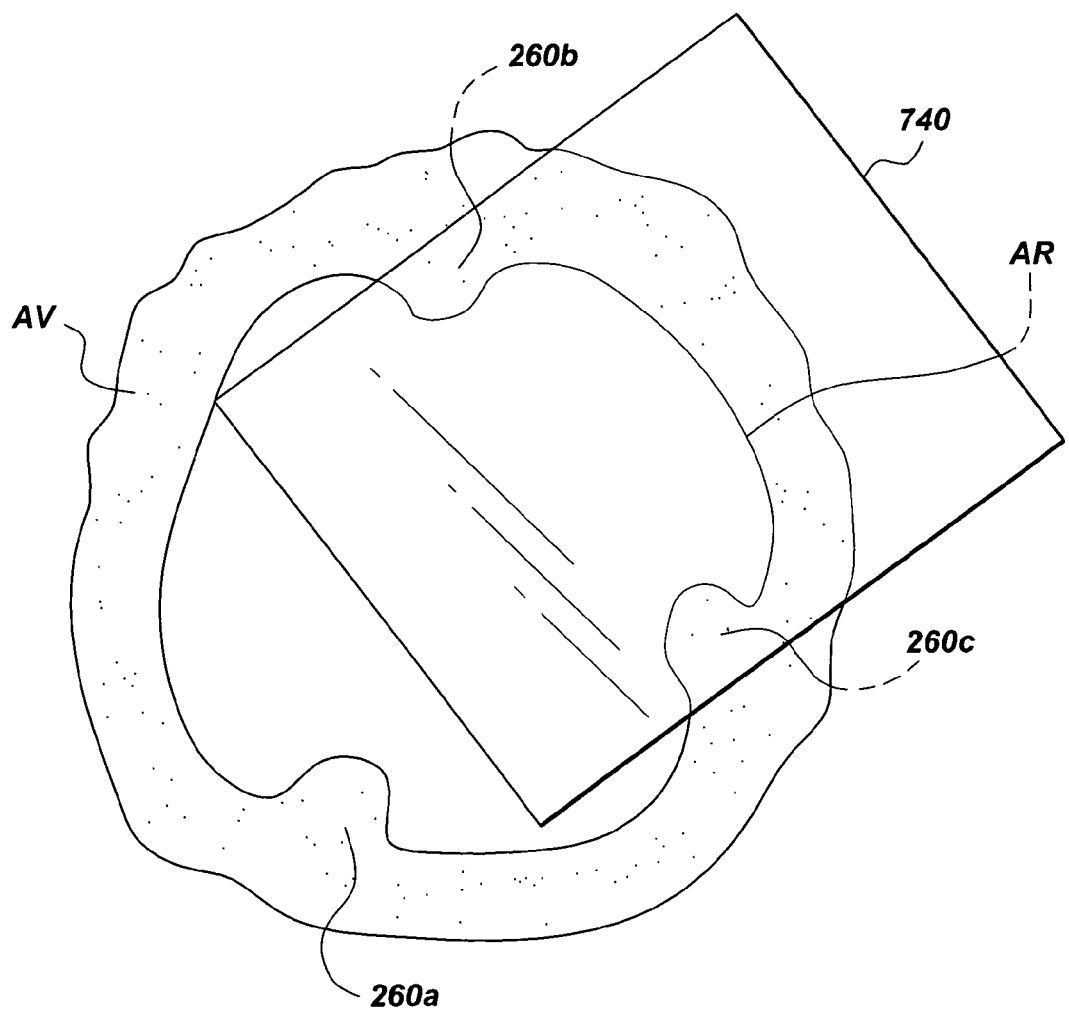
FIG. 27B shows the transparent sheet of FIG. 27A positioned over a surgically opened aortic valve and further positioned over an aortic valve leaflet located between two selected aortic commissures.
Figure 27C:
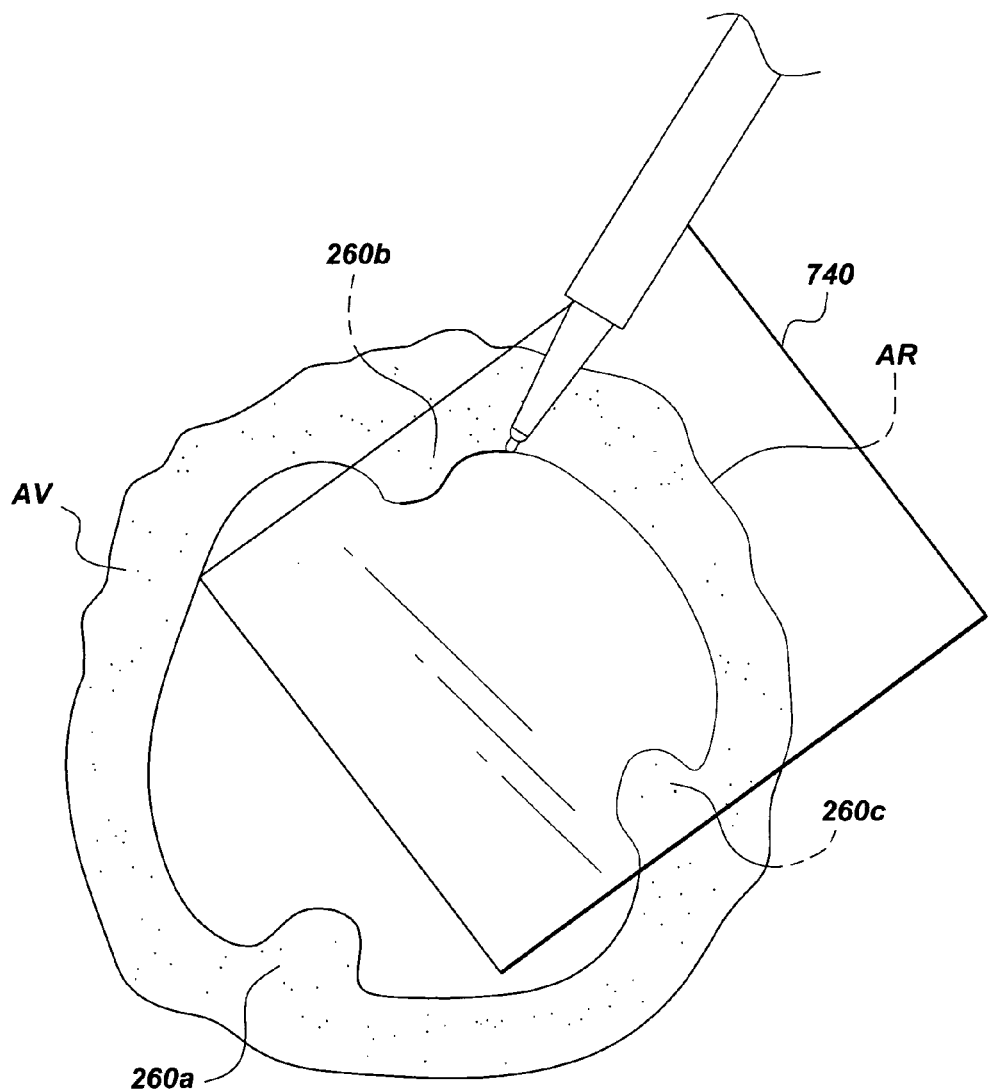
FIG. 27C shows a selected native aortic valve leaflet in the process of being traced out on the transparent sheet of FIG. 27A.
Figure 27D:
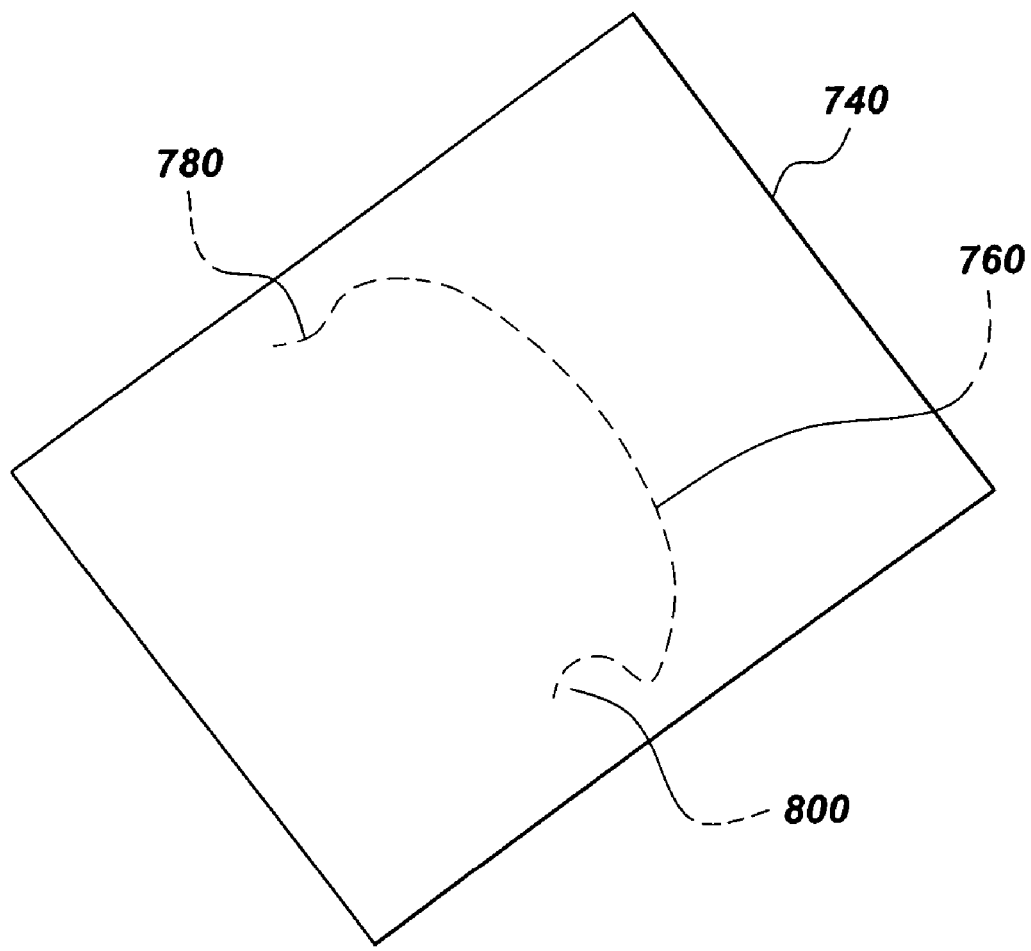
FIG. 27D shows a traced outline of the selected native aortic valve leaflet of FIG. 27C.
Figure 27E:
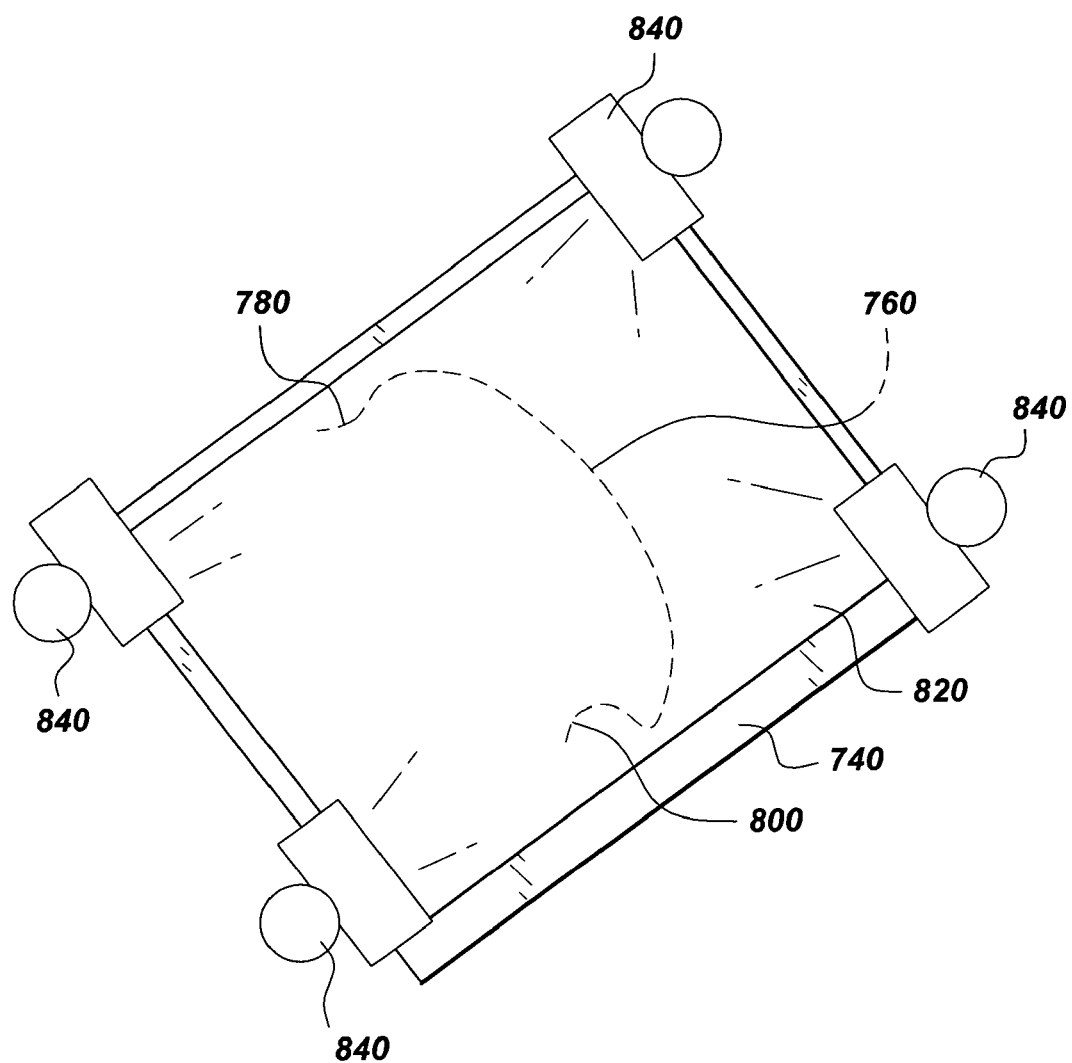
FIG. 27E shows a sheet of pericardium tissue attached to the transparent sheet of FIG. 27A such that the pericardium sheet covers the traced outline of FIG. 27D.
Figure 27F:
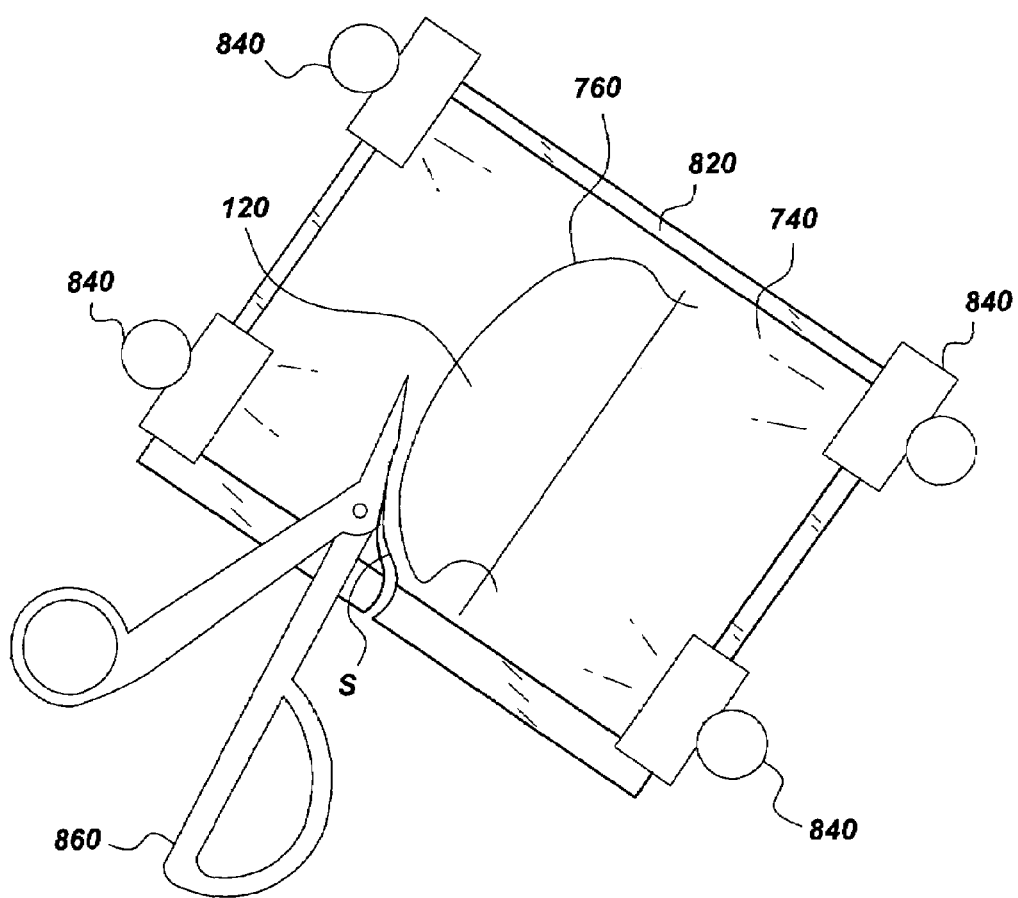
FIG. 27F shows the sheet of pericardium tissue in the process of being cut in response to the traced outline of FIG. 27D.
Figure 27G:
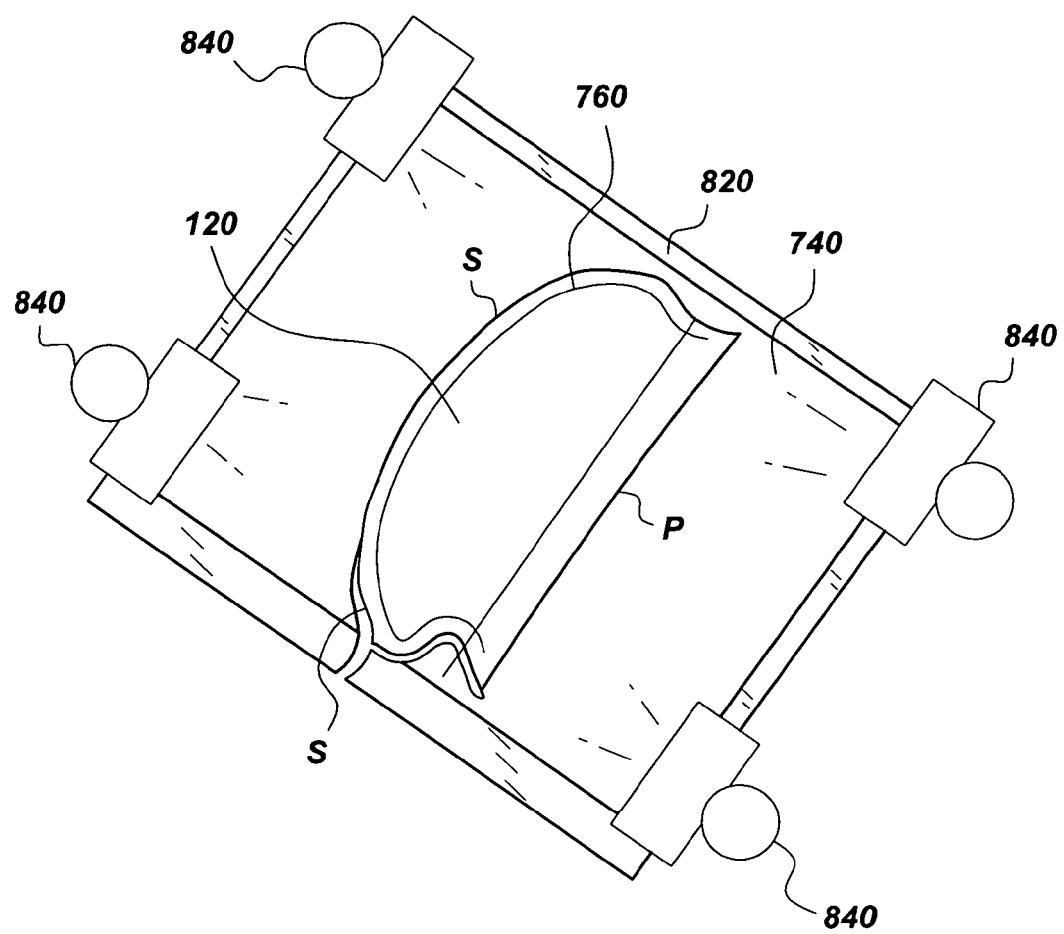
FIG. 27G shows further cutting of the sheet of pericardium tissue of FIG. 27E.
Figure 27H:
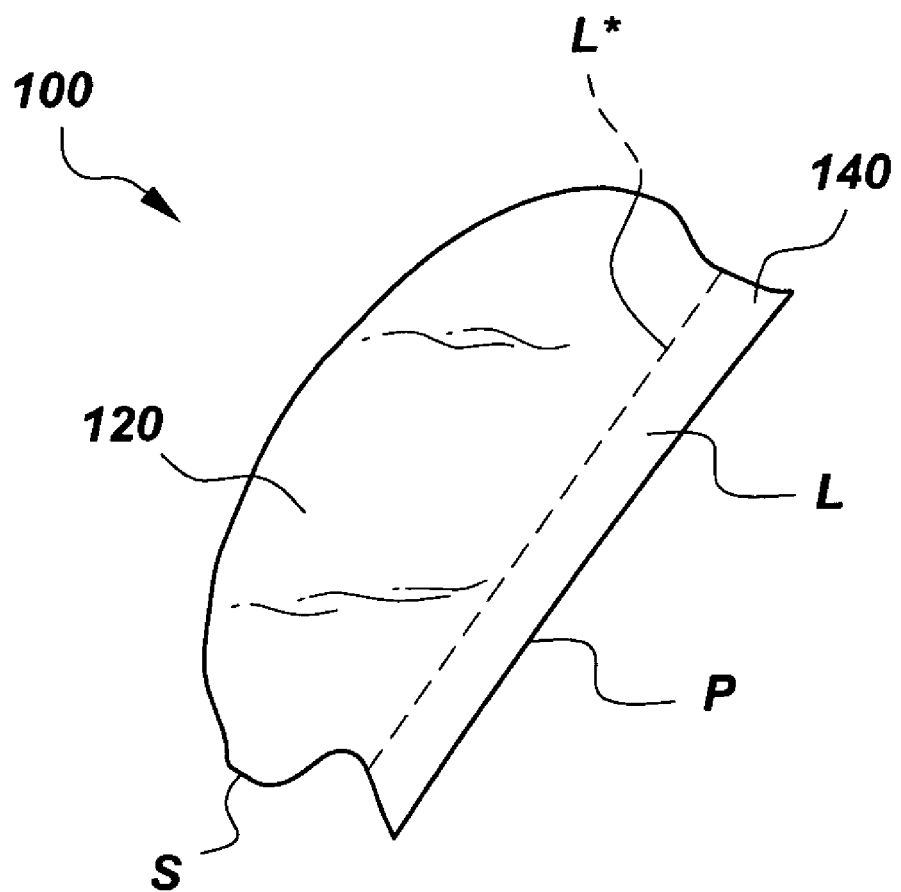
FIG. 27H shows a replacement leaflet cut from the pericardium sheet, according to the present invention.
Figure 27I:
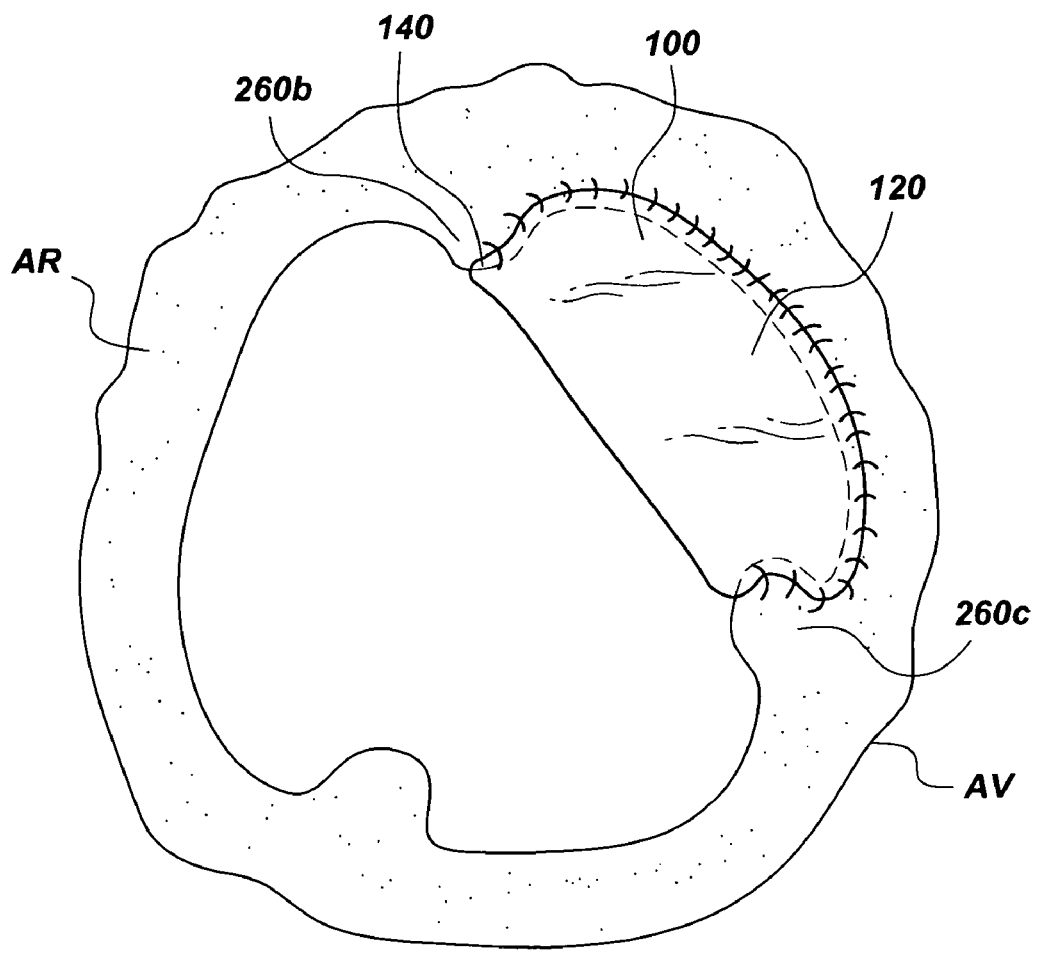
FIG. 27I shows the replacement leaflet of FIG. 27H inserted into a patient's aortic valve.

In yet another embodiment of the present invention, a method is provided for making a replacement leaflet 100 of the present invention, this method comprises the following steps: (i) providing a transparent sheet 740 (see FIG. 27A, transparent sheet 740 is shown not to scale); (ii) placing the transparent sheet 740 over a surgically opened aortic valve AV such that the transparent sheet 740 overlaps two selected aortic commissures 260a and 260b and aortic ring AR found between the two selected aortic commissures 260a and 260b (see FIG. 27B, and for reference see FIG. 3B), (iii) tracing onto the transparent sheet 740 a section of aortic ring AR found between first and second selected aortic commissures 260b and 260c (see FIG. 27C) to provide a traced outline 760 having first and second opposite ends 780 and 800 that overlap the two selected aortic commissures 260a and 260b (see FIG. 27D), wherein the traced outline 760 can be any suitable trace such as, but not limited to, a continuous traced outline, a semi-continuous traced outline or dashed line traced outline; (iv) placing a sheet of pericardium tissue 820 onto the transparent sheet 740 such that the pericardium sheet 820 covers the traced outline 760 (see FIG. 27E), the sheets 740 and 820 are held in place by fasteners such as, but not limited to, staples, small bulldog clips (represented by numeric label 840 in, e.g., FIG. 27E), crocodile clips; (v) cutting the sheet of pericardium tissue 820 approximately along the traced outline 760 to provide a generally curved segment 120 having periphery S, wherein any suitable cutting implement can be used such as a surgical scissors 860 (see FIGS. 27F through 27H); and (vi) cutting and trimming the pericardium tissue sheet 820 ahead of the generally curved segment 120 to provide an overlap segment 140 integral with and adjoining segment 120 (see FIGS. 27G and 27H) to provide a replacement leaflet 100 of the present invention, wherein said overlap segment 140 defines a free borderline periphery P (see FIG. 27H, wherein segments 120 and 140 are, for convenience, shown separated by virtual inter-commissural line L*). The surgeon SU is then free to insert (by suturing and/or stapling) the replacement leaflet 100 to appropriate sections of aortic ring AR between a selected pair of aortic commissures (see FIG. 26I) such as, but not limited to, 260a and 260b.

Figure 28A:
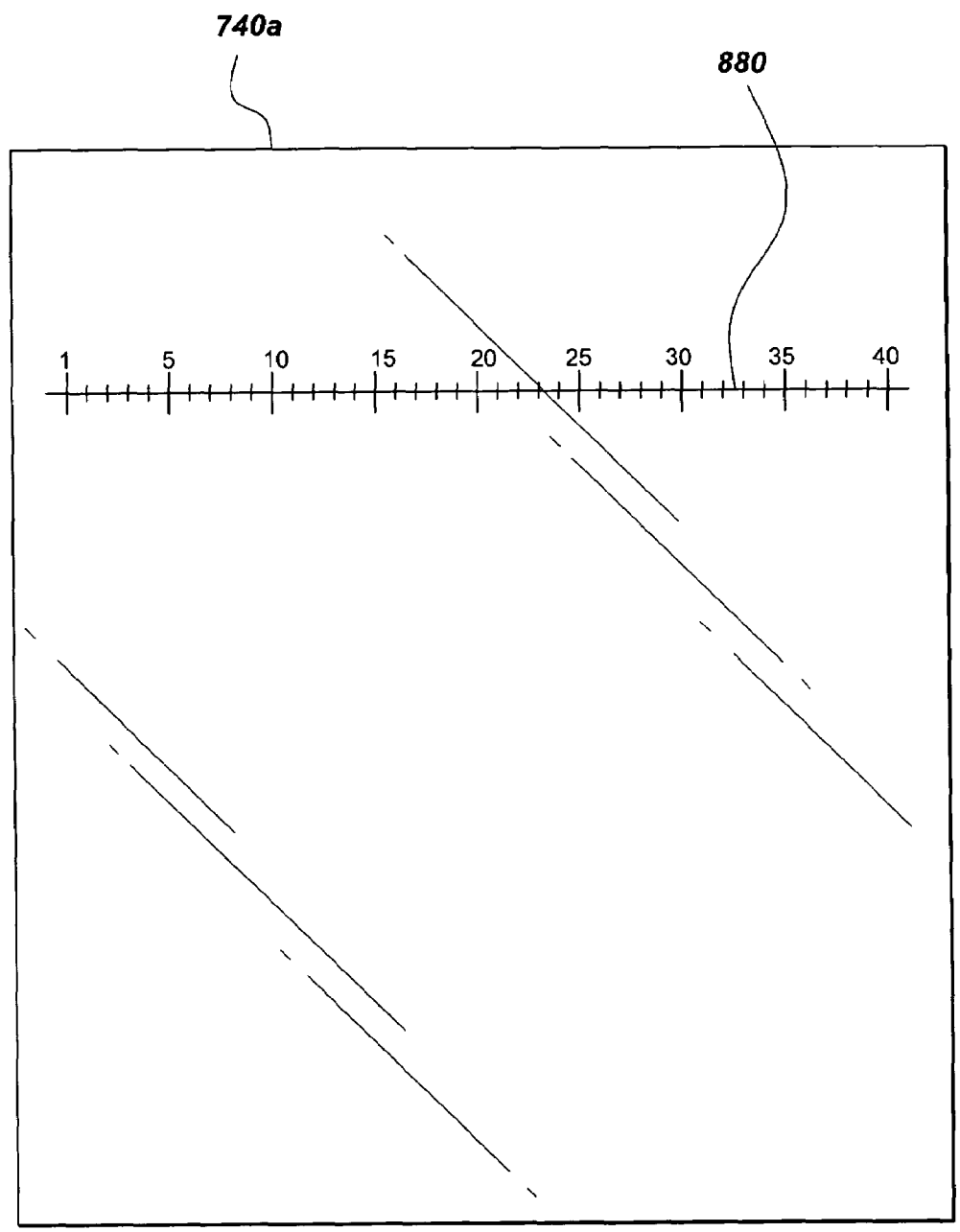
FIG. 28A shows a transparent sheet having a linear line disposed thereon.
Figure 28B:
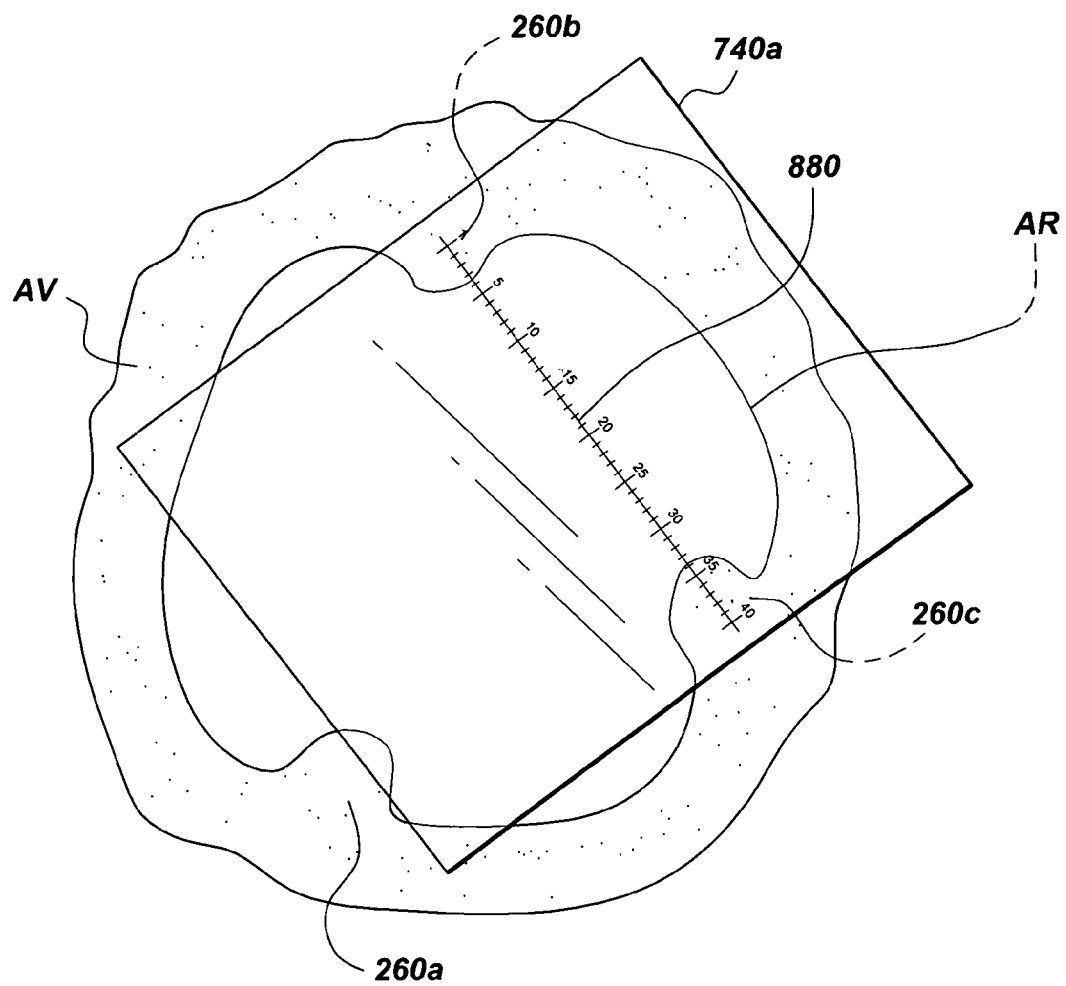
FIG. 28B shows the transparent sheet of FIG. 28A positioned over a surgically opened aortic valve and further positioned over an aortic valve leaflet located between two selected aortic commissures, wherein the linear line is overlaps the two selected aortic commissures.

In yet another embodiment of the present invention, a method is provided for making a replacement leaflet 100 of the present invention, this method comprises the following steps: (i) providing a transparent sheet 740a having a linear line 880 disposed thereon (see FIG. 28A); (ii) placing the transparent sheet 740a over a patient's aortic valve AV such that the linear line 880 overlaps two selected aortic commissures 260b and 260c (see FIG. 28B), (iii) tracing onto the transparent sheet 740a a section of aortic ring AR found between first and second selected aortic commissures 260a and 260b to provide a traced outline 760 having first and second opposite ends 780 and 800 that intersect the linear line 740 (see FIG. 28B); (iv) placing a sheet of pericardium tissue 820 onto the transparent sheet 720 such that the pericardium sheet 820 covers the traced outline 760; (v) cutting the sheet of pericardium tissue 820 approximately along the traced outline 760 to provide a generally curved segment 120 having periphery S; and (vi) cutting and trimming the pericardium tissue sheet 820 ahead of the generally curved segment 120 to provide an overlap segment 140 adjoining segment 120 to provide a replacement leaflet 100 of the present invention, wherein said overlap segment 140 defines a free borderline periphery P. The surgeon SU is then free to insert (by suturing and/or stapling) the replacement leaflet 100 to appropriate sections of aortic ring AR between a selected pair of aortic commissures such as, but not limited to, 260a and 260b.

In another aspect of the invention, a method is provided for making a replacement aortic leaflet 100, comprising the steps of: obtaining a traced outline of a section of aortic ring between two selected aortic commissures located in a surgically opened aortic valve; and cutting a replacement aortic leaflet based on the traced outline to provide a replacement aortic leaflet.

It is to be understood that the present invention is not limited to the embodiments described above, but encompasses any and all embodiments within the scope of the following claims.

What is claimed is:

1. A measuring device for measuring inter-commissural dimension L and the length parameter AM, said device comprises:
    a generally T-shaped member, wherein said T-shaped member comprises:
        an L distance measuring member, wherein said L distance measuring member has first and second opposite ends and a middle section between said first and second opposite ends, wherein said L distance measuring member is less than about 40 mm in length, and wherein numeric measurement indicia are located at said first and second opposite ends of said L distance measuring member; and
        an AM measuring member, wherein said AM measuring member has first and second opposite ends, wherein said first end of said AM measuring member is connected to said middle section of said L distance measuring member thereby defining said T-shaped member, wherein said AM distance measuring member is less than about 40 mm in length and wherein further numeric measurement indicia is located at said second end of said AM measuring member.

2. The measuring device according to claim 1, wherein said L distance measuring member is less than about 30 mm in length.

3. The measuring device according to claim 1, wherein said L distance measuring member is about 25 mm in length.

4. The measuring device according to claim 1, wherein said AM measuring member is less than about 30 mm in length.

5. The measuring device according to claim 1, wherein said AM measuring member is about 25 mm in length.

6. A measuring device for measuring inter-commissural dimension L and the length parameter AM, said device comprising:
    a T-shaped member having a hollow vertical bore and a horizontal arm, wherein said horizontal arm is used for measuring inter-commissural dimension L;
    an AM measuring shaft for measuring the AM length parameter, said measuring shaft is housed in said bore, and wherein said measuring shaft has a lower end; and
    measurement indicia displayed on said shaft for measuring said AM parameter.

7. The device according to claim 6, wherein said shaft defines a lower end, wherein said indicia are displayed on said lower end of said shaft.

8. The device according to claim 6, further comprising a fixator member.

9. The device according to claim 6, wherein said shaft is movable within said bore, and further wherein said fixator holds said shaft in place inside said bore.

* * * * *